US010252966B1

(12) United States Patent
Harvey et al.

(10) Patent No.: US 10,252,966 B1
(45) Date of Patent: Apr. 9, 2019

(54) RENEWABLE POLYPHENOLS, THERMOPLASTICS, AND RESINS

(71) Applicant: THE UNITED STATES OF AMERICA AS REPRESENTED BY THE SECRETARY OF THE NAVY, Washington, DC (US)

(72) Inventors: Benjamin G. Harvey, Ridgecrest, CA (US); Heather A. Meylemans, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 836 days.

(21) Appl. No.: 13/860,975

(22) Filed: Apr. 11, 2013

Related U.S. Application Data

(60) Provisional application No. 61/635,816, filed on Apr. 19, 2012.

(51) Int. Cl.
| | | |
|---|---|---|
| *C04B 26/12* | (2006.01) | |
| *C07C 41/30* | (2006.01) | |
| *C07C 261/02* | (2006.01) | |
| *C07C 41/18* | (2006.01) | |
| *C07C 43/205* | (2006.01) | |
| *C07C 43/23* | (2006.01) | |
| *C08G 64/16* | (2006.01) | |
| *C08G 73/06* | (2006.01) | |

(52) U.S. Cl.
CPC ............. *C07C 41/30* (2013.01); *C07C 41/18* (2013.01); *C07C 43/2055* (2013.01); *C07C 43/23* (2013.01); *C07C 261/02* (2013.01); *C08G 64/1608* (2013.01); *C08G 73/0644* (2013.01); *C08G 73/0655* (2013.01)

(58) Field of Classification Search
CPC ...................................................... C04B 26/12
USPC ............................................................ 524/594
See application file for complete search history.

(56) References Cited

U.S. PATENT DOCUMENTS

| | | | | |
|---|---|---|---|---|
| 5,342,916 A | * | 8/1994 | Weiser ...................... | C14C 3/20 525/497 |
| 2004/0011526 A1 | * | 1/2004 | Berger ................... | C09K 8/584 166/275 |
| 2007/0073090 A1 | * | 3/2007 | More ..................... | C07C 37/20 568/717 |

OTHER PUBLICATIONS

Meylemans et al. "Synthesis of Renewable Bisphenols from Creosol", ChemSusChem, 2012, 5, 206-210. Published online Dec. 12, 2011.*

* cited by examiner

*Primary Examiner* — Jane L Stanley
(74) *Attorney, Agent, or Firm* — Charlene A. Haley

(57) ABSTRACT

A series of renewable bisphenols has been synthesized from creosol (2-methoxy-4-methylphenol) through stoichiometric condensation with short chain aldehydes. Creosol can be readily produced from lignin, potentially allowing for the large scale synthesis of bisphenol A replacements from abundant waste biomass. The renewable bisphenols were isolated in good yield and purity without resorting to solvent intense purification methods. Zinc acetate was shown to be selective catalyst for ortho-coupling of formaldehyde but was unreactive with more sterically demanding aldehydes. Dilute HCl and HBr solutions were shown to be effective catalysts for the selective coupling of aldehydes in the position meta to the phenol. Acid solutions could be recycled and used multiple times without decreases in activity or yield.

17 Claims, 8 Drawing Sheets

US 10,252,966 B1

RENEWABLE POLYPHENOLS, THERMOPLASTICS, AND RESINS

CROSS-REFERENCE TO RELATED APPLICATIONS

This is a non-provisional patent application, claiming the benefit of, parent application Ser. No. 61/635,816 filed on Apr. 19, 2012, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to the synthesis of bio-polyphenols, and more particularly, converting renewable phenols to thermoplastics, resins, and composite materials.

Figure 1:
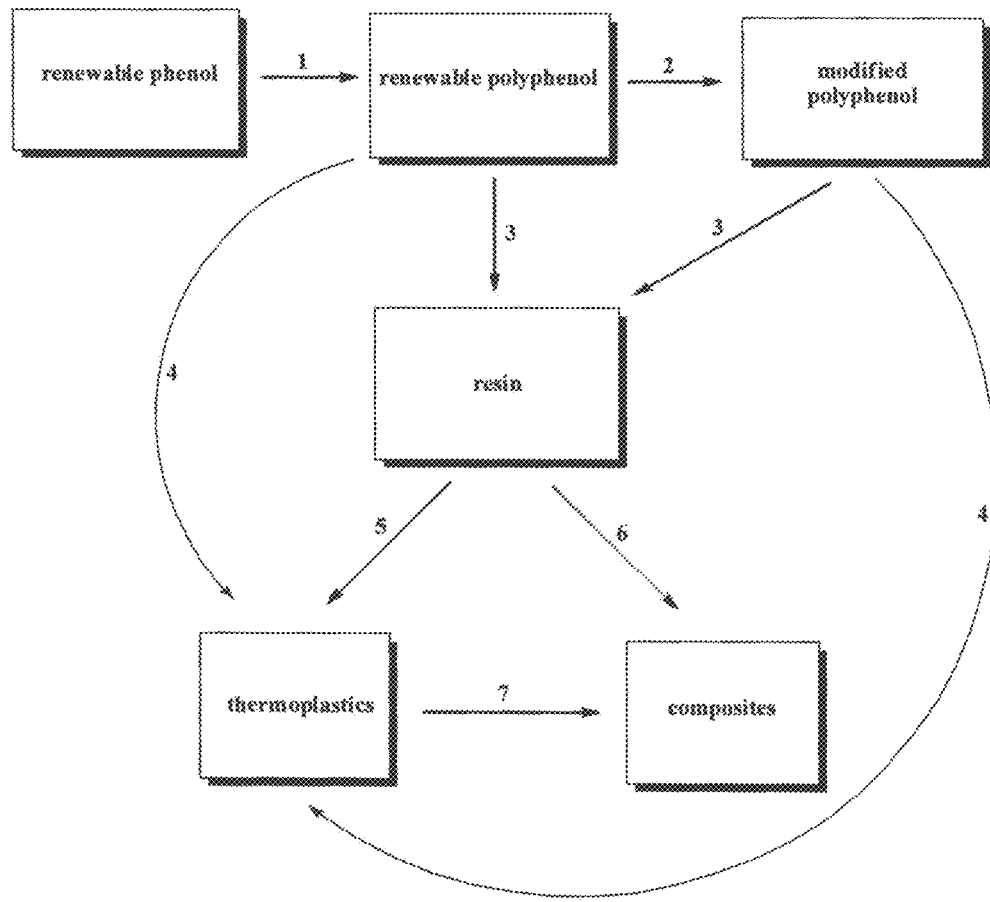
FIG. 1 is a diagram showing a series of renewable bisphenols derived from renewable phenols and the resins, thermoplastics, and composite materials produced according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to the synthesis of bio-polyphenols, and more particularly, converting renewable phenols to thermoplastics, resins, and composite materials.

The efficient and selective synthesis of bisphenols from renewable materials and the subsequent conversion of these phenols to a variety of polymers and resins represent a major breakthrough in the production of renewable composite materials. Renewable phenols can be converted to thermoplastics and resins with uses across a wide range of Navy platforms. In addition to reducing dependency on petroleum sources for structural materials, increased use of lightweight plastics and composites reduces overall fuel usage, reducing Navy costs. Preparation of a bisphenol from creosol by condensation with formaldehyde at the ortho-phenolic position is described in the following patent: [Bailey, H. C. GB845608 (1960)]

Bisphenol compounds such as BPA (bisphenol A) are widely used as building blocks for a variety of commercial and industrial products. Specifically, bisphenols are the building blocks for polycarbonate plastics, epoxy resins, polyester resins, cyanate ester resins and other plastics which include but are not limited to polysulfone, polyesterstyrene, alkylphenolic, and polyalylate functionalities. Commercially available bisphenol compounds, especially polyaromatic bisphenols, are currently derived from petroleum. In an effort to create more sustainable bisphenol building blocks a series of polyaromatic bisphenol compounds have been synthesized from creosol. Creosol, a reduced form of vanillin is a compelling feedstock for the synthesis of bisphenols. The large scale isolation of vanillin from lignin is a demonstrated commercial process and a straightforward hydrogenation of vanillin has been show to produce creosol in 99% yield. Condensation of creosol with short chain aldehydes has the potential to produce bisphenols that can be converted to resins with tunable physical characteristics including melting points, hydrophobicity, and toughness. The utilization of renewable polyphenols as precursors to epoxies, polycarbonates, and high temperature thermosets including cyanate esters, provides an opportunity to develop full-performance resins while reducing the use of petroleum based feedstocks. This approach will then diminish the overall environmental impact of resin production while allowing for a sustainable source of phenols. As a tangential benefit, renewable phenols may have significantly lower toxicity than typical precursors such as bisphenol A.

Embodiments of the invention include the following tasks shown in FIG. 1: Task 1: A renewable phenol (e.g. guaiacol, creosol (2-methoxy-4-methylphenol), the three structural isomers of cresol) is converted to a polyphenol through condensation with an alehyde using either Bronsted or Lewis acids, in either a homogenous or heterogeneous fashion; Task 2: Depending on the properties of the polyphenol, the molecule is selectively modified through elimination and/or hydrolysis to yield an altered polyphenol; Task 3: Polyphenols prepared in either Task 1 or Task 2 are converted to a variety of resins (e.g., cyanate esters, epoxides); Task 4: Alternatively, polyphenols prepared in either Task 1 or Task 2 are directly converted to thermoplastics such as polycarbonates; Task 5: In specific cases, resins are polymerized to form high molecular weight thermoplastics; Task 6: Resins are combined with fibers (e.g. glass, carbon) or other support materials and cured through various methods to produce a composite material; Task 7: Thermoplastics produced in Task 4 are either utilized in a pure form or are combined with a support material to produce a composite.

Other embodiments of the invention include the following tasks: Task 1: A biphasic reaction mixture comprised of a renewable phenol, a stoichiometric amount of aldehyde, and a dilute mineral acid solution is heated for several hours to yield a bisphenol. The acid solution can be reused several times without affecting the yield or purity of the product. Several examples are presented in the following pages and supporting information. In some cases a homogenous or heterogeneous Lewis acid catalyst can also be used; Task 2: To alter the properties of the bisphenol and subsequent resins and polymers, the phenols can be eliminated through conversion of the phenol to a mesylate or triflate followed by reductive elimination. Residual methoxy groups in the renewable phenols are then readily hydrolyzed to produce new bisphenols with different properties. Specific examples are included in the supporting information; Task 3: Polyphenols can be readily converted to cyanate esters, epoxides, and other resins of interest. A general synthesis for the renewable cyanate esters is included in the supporting information; Task 4: Thermoplastics are readily prepared from renewable polyphenols. Specifically, polycarbonates are isolated by reaction of the phenols with diphenylcarbonate and a zinc catalyst. An example of this synthesis is included in the supporting information.

In recent years, a myriad of approaches have been developed for the efficient conversion of biomass to both custom chemicals and fuels. ((a) Climent, M. J., Comna, A., Ibarra, S. *Green Chem.* 2011, 13, 520-540. b) Sheldon, R. A. *Catalysis Today* 2011, 167, 3-13. c) Ragauskas, A. J., Williams C. K.; Davison, B. H.; Brrtovsek, G.; Caimey, J., Eckert, C. A.; Frederick, W. J.; Hallett, J. P., Leak, D. J.; Liotta, C. L.; Mielenz, J. R.; Murphy, R., Templer, R., Tschaplinski, T. *Science* 2006, 311, 484-489) In parallel with these efforts, routes to renewable and sustainable polymer systems have been investigated and in some cases, commercialized. (Renewable and Sustainable Polymers: Payne, G. F., Smith, P. B., Eds.; ACS Symposium Series 1 063; American Chemical Society: Washington, DC, 2011; pp 1-212) Although triglycerides and cellulose have been examined as the preferred feedstocks for many of these polymers, well-defined polymers from lignin have been largely unexplored, likely due to the difficulty of isolating pure, well-defined monomers on a large scale. (Gandini, A. *Macromolecules* 2008, 41, 9491-9504)

Given the obvious benefits of highly aromatic polymer systems, including good thermal and mechanical properties, the study of methods for the efficient utilization of lignin has the potential to yield industrially relevant quantities of renewable polymers that meet the demanding requirements of conventional aromatic based resins (Lindberg, J. J.; Kuusela, T. A., Levan, K. *ACS Symp. Ser.* 1989, 397, 190-204 b) Hatakeyama, H., Hirose, S.; Hatakeyama, T. *ACS Symp. Ser.* 1989, 397, 205-218) The utilization of renewable polyphenols as precursors to epoxies, polycarbonates, and high temperature thermostats such as cyanate esters, provides an opportunity to develop full performance resins while reducing the use of petroleum based feedstocks. This approach will then diminish the overall environmental impact of resin production while allowing for a sustainable source of phenols. As a tangential benefit, renewable phenols may have significantly lower toxicity than typical precursors such as bisphenol A (Nouailhas, H.; Aouf, C.; Le Guemeve, C.; Caillol, S.; Boutevin, B.; Fulcrand, H. *J. Polym. Sci. Part A* 2011, 49, 2261-2270)

Creosol, a reduced form of vanillin (Scheme 1) is a compelling feedstock for the synthesis of bisphenols. The large scale isolation of vanillin from lignin is a demonstrated commercial process (Hocking, M. B. *J Chem. Edu.* 1997, 74, 1055-1059) and a straightforward hydrogenation of vanillin has been shown to produce creosol in 99% yield (Wang, Q.; Yang, Y.; Li, Y.; Yu, W.; Hou, Z. J *Tetrahedron* 2006, 62,6107-6112) Condensation of creosol with short chain aldehydes has the potential to produce bisphenols that can be converted to resins with tunable physical characteristics including me t ng points, hydrophobicity and toughness. The methyl group in creosol effectively blocks the position para to the phenol, while the phenol and methoxy groups direct coupling to positions A and B, respectively (Scheme 1). Thus, although renewable phenols often have additional functional groups on the aromatic r ng, the steric hindrance and directing effects of these groups can in some cases be utilized to control product distributions.

Scheme 1. Synthesis of creosol from lignin

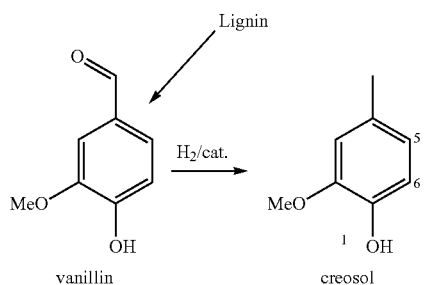

Scheme 2. Synthesis of Bisphenol A (BPA)

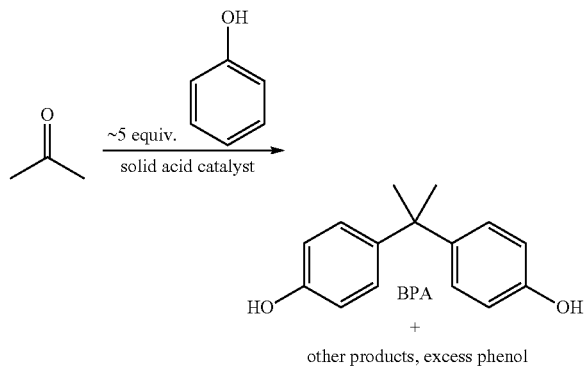

In contrast, aldehyde and ketone condensation reactions with phenol must be run at a high phenol:aldehyde/ketone ratio in order to reduce side products including o.p-bisphenols and novolac type resins (Scheme 2) (Yadav, G. D., Kirthivasan, N. *Appl. Catal. A.* 1997, 154, 29-53).

As an example of the low selectivity of substituted phenols in aldehyde condensation reactions, a total of six isomers are isolated when a 50:1 ratio of 3-methylphenol to formaldehyde is allowed to react. (Bogan, L. E., Wok, S. K. *Macromolecules* 1992, 25, 161-165) In the special case of renewable materials, atom economy is at a premium, making a stoichiometric process much more favorable. In this report we describe the efficient, selective, and stoichiometric synthesis of bisphenols from creosol.

Synthesis of Bisphenols

As an initial entry into this chemistry, we sought to condense one equivalent of an aldehyde or ketone with two equivalents of creosol. In an effort to reduce the environmental impact of the process, we first evaluated Nafion as a heterogeneous acid catalyst for the condensation reactions. Surprisingly, Nafion was ineffective at catalyzing the condensation reaction between creosol and formaldehyde, acetaldehyde, propionaldehyde, and acetone, respectively. Regardless of the aldehyde or ketone used, no reaction was observed even at temperatures in excess of 100° C. Next, a Lewis Acid catalyst, Zn(Ac)2 was used at very modest loadings (0.8 mol%) and the ortho-coupled product, 6,6'methylenebis(2-methoxy-4-methylphenol) (2) (J Bailey, H. C. GB8456081960) was isolated in reasonable yield. Zn(11) has been shown to be selective for ortho condensation products based on a chelating effect (Fraser, D. A.; Hall, R. W.; Jenkins, P. A.; Raum, A. L. J. J. Appl. Chem. 1957,7,689-700) and (2) was the only observed product. Although it has been suggested (J Bailey, H. C. GB8456081960) that other simple aldehydes such as acetaldehyde can be effectively condensed with creosol using this method, no reaction was observed with either acetaldehyde or propionaldehyde, even after 72 h at reflux and up to ten times the standard catalyst loading. Turning to Bronsted acid catalysts, we explored the use of biphasic systems consisting of mineral acids and creosol for the synthesis of bisphenols (Scheme 4). (For similar procedures, see for example: a) Sverker Hogberg, A. G. *J. Org. Chem.* 1980, 45, 4498-4500. b) Zhou, Y., Jiang, C.; Zhaug, Y.; Liang, Z.; Liu, W., Wang, L.; Luo, C.; Zhong, T.; Sun, Y.; Zhao, L.; Xie, X., Jiang, H.; Zhou, N., Liu, D.; Liu, H. *J. Med. Chem.* 2010, 53, 5449-5466) 2.5 M HCl was determined to be the most effective catalyst for the condensation of creosol with formaldehyde. (Area leo, A., Garofana, T. *Annali di Chimica* 1957, 47, 1141-1162) In contrast to the zinc catalyzed reaction, formaldehyde coupled almost exclusively at the position meta to the phenol with a selectivity of 97%. As opposed to acid catalyzed condensation of simple phenol with formaldehyde, the steric constraints of creosol along with the para-directing and ortho-directing effects of the methoxy and methyl groups, respectively, resulted in the product specificity. In a similar manner, the stoichiometric condensation product of creosol and acetaldehyde (4) was prepared in 68% yield (Table 1). Propionaldehyde proved to be a much more demanding substrate than acetaldehyde (Compound 5 has been reported as the condensation product using dilute $H_2SO_4$, as a catalyst: Yasuda, S.; Ota, K. *Mokuzai Gakkaishi* 1986, 32, 51-8. However, in our laboratory, dilute $H_2SO_4$, did not promote the condensation of creosol and propionaldehyde) and could not be condensed even with concentrated HCl. 5 M $H_2SO_4$ also produced no reaction, while 9 M and concentrated $H_2SO_4$ produced black solutions with multiple products. Although the dark color suggested the presence of quinones, concentrated $H_2SO$ has been reported to convert aryl methyl ethers to phenols, which may further complicate the product distribution. (Burwell, R. L. *Chem. Rev.* 1954,54, 615-683) Interestingly, 6 M HBr cleanly produced bisphenol (5) in 67% yield at room temperature. This is likely the result of enhanced reactivity of the intermediate carbocation due to the greater polarizability of bromide compared to chloride.

TABLE 1

Synthesis of Bisphenols from Creosol

| Product | Catalyst | Yield (%) |
|---|---|---|
| 2 | Zn(Ac)2 | 41[a] |
| 3 | 2.5M HCl | 63[b] |
| 4 | 2.5M HCl | 68[c] |
| 5 | 6M HBr | 67[d] |

[a] 0.8 mol % catalyst, 16 h, reflux.
[b] 3 h, reflux.
[c] 4 h, reflux, phenol:aldehyde ratio of 1.5.
[d] 16 h, ambient Scheme 3. Proposed mechanism for Zn(Ac)2 mediated coupling of creosol with formaldehyde.

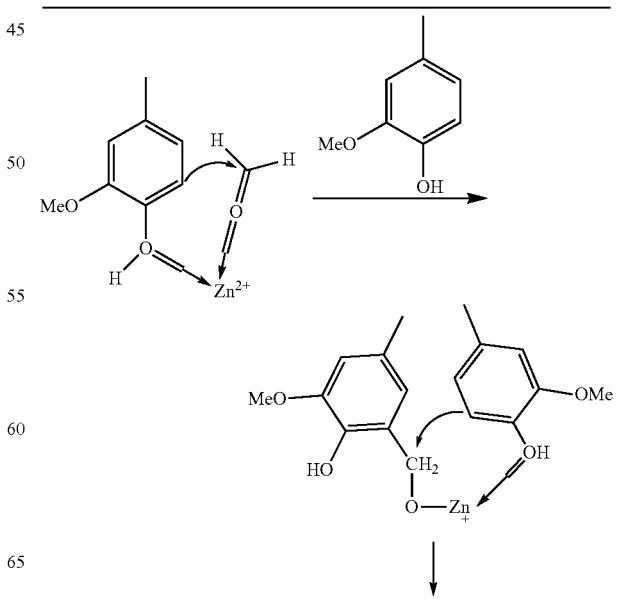

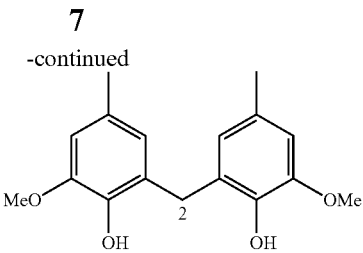

Scheme 4. Bronsted acid catalyzed coupling of creosol with aldehydes.

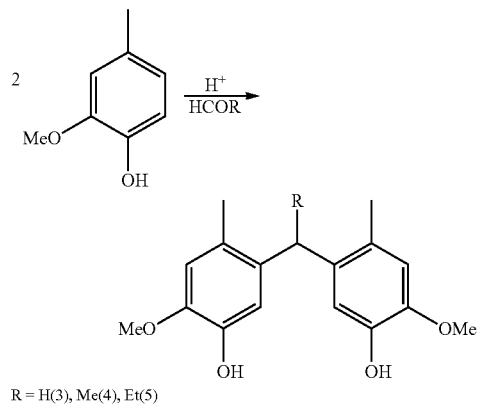

R = H(3), Me(4), Et(5)

The meta,meta isomers were produced almost exclusively regardless of the aldehyde (Table 2) No significant difference in the selectivity was observed between formaldehyde and acetaldehyde, but when propionaldehyde was condensed, no trace of the meta,ortho product was observed. This suggests that in addition to electronic and steric effects inherent to the phenol, the alkyl group on the aldehyde plays a role in the selectivity of the reaction.

TABLE 2

Selectivity of aldehyde coupling reactions with creosol

| Aldehyde | m,m (%)[a] | m,o (%)[b] |
|---|---|---|
| $CH_2O$ | 97 | 3 |
| $CH_3CHO$ | 96 | 4 |
| $CH_3CH_2CHO$ | 100 | — |

[a]meta,meta isomer
[b]meta,ortho isomer

The biphasic approach to bisphenol synthesis has a number of advantages over conventional techniques. The initial reaction requires no organic solvent and the crude product can be isolated by a simple decantation followed by a water wash. Although subsequent steps utilize solvents for purification, the phenols can also be purified by sublimation, resulting in a solvent free process. In addition, the procedure is carried out at modest temperatures and does not require protection from atmospheric conditions. Perhaps one of the most attractive aspects of this method is the potential to reuse the acid solutions. To examine the feasibility of recycling the acid solutions, (4) was prepared according to the standard conditions with 2.5 M HCl. The acid solution was then reused in two subsequent reactions without any purification. The yields actually increased slightly in later reactions, perhaps due to residual reagents that were solubilized in the aqueous phase. Although from an initial standpoint the use of mineral acids may be considered detrimental for a sustainable process, the ability to reuse the acid solutions greatly reduces the environmental impact of this approach.

Structures and Properties of Bisphenols

Figure 2:
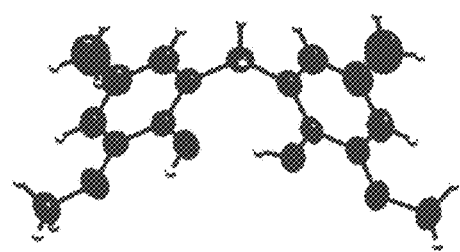
FIG. 2 is a perspective view of a solid state structure of compound 3, according to embodiments of the invention.
Figure 3:
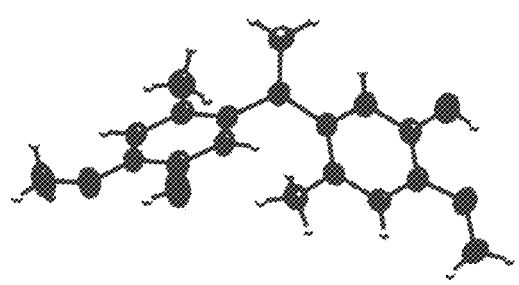
FIG. 3 is a perspective view of compound 4, according to embodiments of the invention.

In order to confirm the structures and evaluate the suitability of various phenols as precursors to thermoplastics and thermosetting resins, X-ray structures for each of the bis-phenols were determined (Structural data for 2, 3, 4, and 5 have been deposited in the Cambridge Structural database; deposition numbers 831799, 831800, 831801, and 831802, respectively). Compound 2, in addition to exhibiting intermolecular hydrogen bonding has two intramolecular hydrogen bonds of 1.83(2) and 2.24(2) Å between the hydroxyl groups and between a hydroxy and methoxy oxygen, respectively. This interaction is allowed by the close proximity of the phenols resulting from the ortho coupling and results in a symmetrical molecule in the solid state (FIG. 2). The bisphenols substituted at the meta position also engage in intramolecular hydrogen bonding but the aromatic substitution precludes the strong interring hydrogen bonding observed in (2) and results in rotated aromatic groups; as an example, compound (4) is shown in FIG. 3. (The angles between rings are 78.18, 81.49, and 72.34° for 3, 4, and 5, respectively) In contrast to the other phenols, pure 5 was isolated as an oil at room temperature. Although $^{13}C$ NMR spectroscopy and GC/MS confirmed the purity of this oil, $^1H$ NMR spectroscopy revealed the presence of residual water even after extended drying in a vacuum oven. This excess water was confirmed by elemental analysis and on this basis we proposed that the oil is a water adduct of 5 with a stoichiometry of 5·1.5 $H_2O$. In the presence of DMSO, 5 formed a solvent adduct that readily crystallized, allowing for structural comparison. The adduct is stabilized by a strong hydrogen bonding interaction between the phenol and DMSO. One of the goals of this research was the development of a series of renewable phenols that could be selectively modified to alter both the hydrophobicity and melting points of the phenols. Daughter resins (e.g. cyanate esters) will in large part inherit the properties of the parent phenols and the current work allows for the resin properties to be custom tailored based on the choice of aldehyde and the condensation catalyst. 2 had the lowest melting point at 123-125° C., followed by 3 at 131-134° C. and 4 at 143-146° C. The increase in melting point from 3 to 4 is surprising when compared to the melting points of the related bisphenol F and bisphenol E at 162-164° C. and 123-127° C. respectively.

In fact, the 1,1-diphenylethane framework typically results in depressed melting points when compared to methylene or 2,2-diphenylpropane linkages. (Cambrea, L. R., Davis, M, C.; Groshens; T. J.; Guenthner, A. J.; Lamison, K. R.; Mabry, J. M. *J. Poly Sci. Part A* 2010, 48, 4547-4554) Despite this discrepancy, upon extension from acetaldehyde to propionaldehyde, the melting point exhibited a drastic decrease and (5) was isolated as a viscous oil. For applications as precursors to thermosetting composites, lower melting resins should allow for simplified, lower cost fabrication methods.

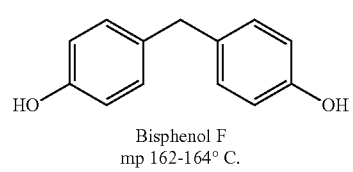

Bisphenol F
mp 162-164° C.

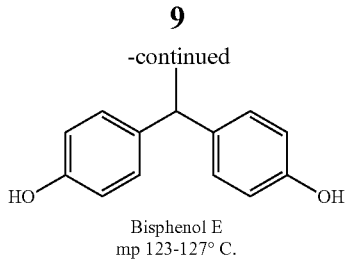

Bisphenol E
mp 123-127° C.

In summary, a series of bisphenols has been synthesized from creosol, a renewable phenol that can be produced from abundant waste lignin. The functional groups on the ring and choice of catalyst allow for exquisite control of the condensation products and these reactions can be conducted with stoichiometric amounts of the phenol. The ability to recycle the acid catalysts, conduct the reaction in the absence of organic solvents, and the potential for the product bisphenols to have lower toxicity than bisphenol A make these phenols intriguing renewable and sustainable precursors to a variety of polymeric materials.

Embodiments of the invention generally relate to methods of synthesizing bio-polyphenols including, condensing one equivalent of an aldehyde and/or ketone with two equivalents of at least one renewable phenol and utilizing at least one dilute mineral acid or heterogeneous solid acid catalyst to produce renewable bio-bisphenols (bio-polyphenols). Another embodiment of the invention relates to further including modifying the renewable bio-bisphenols with sulfonates, followed by reductive elimination and/or hydrolysis methods to yield modified bio-bisphenols (bio-polyphenols). Other aspects of the invention include further converting the renewable bio-bisphenols or the modified bio-bisphenols into resins and polymers including cyanate esters, epoxides, polyesters, polysulfones, polyester-styrene, alkylphenolic polymers, polyoxalates, and polyalylates. This converting process depends on the resin utilized. For cyanate esters this would entail reaction with cyanogen bromide and base at low temperature. For epoxy resins it would require reaction with epichlorohydrin—other resins would require different reagents and conditions.

Yet other aspects of the invention generally relates to further converting either renewable bio-bisphenols and/or modified bio-bisphenols to a polycarbonate with reagents that include organic carbonates (example: diphenylcarbonate) and a Lewis acid catalyst, or other methods known in the art including reaction with phosgene or phosgene surrogates, to produce either linear or cyclic oligomeric polycarbonates and/or high molecular weight polycarbonates with $M_a$ ranging from 1000 to 10,000,000 g/mol. Still yet other aspects of the invention generally relate to further polymerizing by thermal or chemical methods or with irradiation to produce high molecular weight thermoplastics. Other embodiments of the invention relate to further cross-linking the resins with fibers comprises of at least one glass, carbon, polymer, aramid or other support materials that include at least one metal, silica, clay, metal oxide, carbon nanotubes, graphenes, and nanostructured materials to produce a mixture, curing the mixture to produce composite materials. Other embodiments further include utilizing the thermoplastics in a pure form or combined with at least one support material that include at least one of other polymers, aramid fibers, glass, carbon, metals, silica, clays, metal oxides, carbon nanotubes, graphenes, and nanostructured materials produce composite materials. Yet other embodiments further include utilizing the thermoplastics in a pure form or combined with at least one support material that include at least one other polymers, aramid fibers, glass, carbon, metals, silica, clays, metal oxides, carbon nanotubes, graphenes, and nanostructured materials to produce a composite material.

Embodiments of the invention include at least one renewable phenol is selected from the group consisting of creosol (2-methoxy-4-methylphenol), guaiacol (2-methoxyphenol), ortho-cresol, para-cresol, meta-cresol, and any combination thereof. In other embodiments, the sulfonates include at least one mesylate, triflate, and any combination thereof. In embodiments, the heterogeneous solid acid catalyst includes at least one Bronsted and/or Lewis acid sites.

Other embodiments include bio-polyphenols (renewable bio-bisphenols) and modified bio-bisphenols (bio-polyphenols) produced by the methods herein. Embodiments of the invention include cyanate esters, epoxides, and other resins produced by the methods herein. Other embodiments include polycarbonates and other thermoplastics produced by the methods in herein. Yet other embodiments include high molecular weight thermoplastics produced by the methods herein. Still yet other embodiments include composite materials produced by the methods herein. Furthermore, embodiments of the invention include blends of bisphenols/polyphenols produced by the methods herein.

Experimental:

2-methoxy-4-methylphenol (creosol (I)), acetaldehyde, propionaldehyde, formaldehyde (37%), Zn(Ac)2·2H$_2$O, and concentrated HBr (48%) were all purchased from Aldrich and used as received. Concentrated HCl and H$_2$SO$_4$ were purchased from Fisher Scientific and used as received. All NMR data were collected on a Bruker A vance II 300 MHz NMR. NMR samples of bisphenols were prepared in DMSO-d$_6$ and spectra were referenced to the solvent peak (2.50 and 39.5 ppm for $^1$H and $^{13}$C NMR, respectively). Products were further analyzed with an Agilent 6890-GC system with a Restek RTX-5MS 30-meter column. The GC inlet temperature was 250° C. and the column oven temperature program began at 40° C. for three minutes and increased to 350° C. at 10° C./min. An Agilent mass selective detector (MSD) 5973 system was used to identify the sample. All elemental analyses were carried out by Atlantic Microlabs Inc. Norcross, GA.

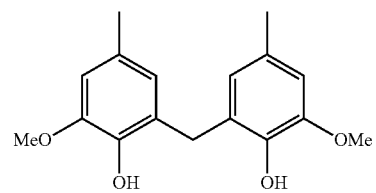 [SMILES: COc1cc(C)cc(Cc2cc(C)cc(OC)c2O)c1O]

6,6'-methylenebis(2-methoxy-4-methylphenol) (2)

5 g of 1 (36.2 mmol), 1.56 g of 37% formaldehyde (19.2 mmol) and 70 mg of Zn(ac)$_2$·2H$_2$O (3.2×10$^{-4}$ mol) were refluxed overnight under N2. The resulting oil was washed with 10% EtOH, and extracted with ether. The ether was removed under reduced pressure and the resulting oil was heated to 100° C. overnight under vacuum. The resulting solid was dissolved in ether and precipitated with heptane. The light tan solid was filtered, washed with excess heptane and dried to yield 2.13 g (41%). $^1$H NMR (d$_6$-DMSO) δ: 2.11 (s, 6H), 3.71 (s, 2H), 3.74 (s, 6H), 6.35 (d, 2H, J=2Hz), 6.58 (d, 2H, J =2Hz), 8.20 (s, 2H). $^{13}$C NMR (d$_6$-DMSO) δ: 21.1 , 29.0, 56.2, 110.7, 122.7, 127.4, 127.7, 141.9, 147.5.

MP: 123-125° C., MS: m/z: 288, 271, 255, 239, 212, 195, 165, 138, 121, 105. EA Calcd. (found): C 70.81 (70.84), H 6.99 (7.13).

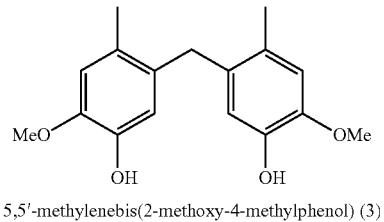

5,5'-methylenebis(2-methoxy-4-methylphenol) (3)

5.03 g of 1 (36.4 mmol) and 1.47 g of 37% formaldehyde (18.1 mmol) were diluted in 40 mL of H$_2$O. 10 ML of concentrated HCl were slowly added and the reaction was refluxed under N$_2$ for 3 hours. A precipitate formed, the solution was decanted and the solid washed with a 10% EtOH solution. The solid was dissolved in ether and precipitated with heptane 3.29 g of crystalline white solid was isolated (63%). Crystals suitable for an X-ray diffraction study were obtained from slow evaporation of ether at room temperature. $^1$H NMR (d$_6$-DMSO) δ: 2.08 (s, 6H), 3.56 (s, 2H), 3.71 (s, 6H), 6.30 (s, 2H), 6.72 (s, 2H), 8.54 (s, 2H). $^{13}$C NMR (d$_6$-DMSO) δ: 19.0, 35.0, 56.2, 115.0, 117.0, 126.3, 131.3, 144.8, 146.6. MP: 131-134° C., MS m/z: 288, 273, 257, 241, 227, 213, 195, 181, 165, 150. EA Calcd. (found): C 70.81 (70.66), H 6.99 (7.16).

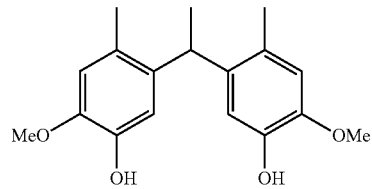 [SMILES: COc1cc(C)c(C(C)c2cc(O)c(OC)cc2C)cc1O]

5,5'-(ethane-1,1-diyl)bis(2-methoxy-4-methylphenol) (4)

5.1 g of 1 (37.0 mmol) and 1.06 g of acetaldehyde (24.1 mmol) were diluted in 40 mL of H$_2$O. 10 mL of conc HCl was slowly added and then reaction was refluxed under N$_2$ for 4 hours. The supernatant was carefully decanted from the resulting dense oil. 3.74 g of white solid was obtained through extraction with ether and precipitation with heptane (68%). Crystals suitable for an X-ray diffraction study were obtained from slow evaporation of ether at room temperature. $^1$H NMR (d$_6$-DMSO) δ: 1.30 (d, 3H, J=7Hz), 2.06 (s, 6H), 3.69 (s, 6H), 4.05 (t,1H, J=7Hz), 6.48 (s, 2H), 6.66 (s, 2H), 8.57 (s, 2H). $^{13}$C NMR (d$_6$-DMSO) δ: 18.5, 21.3, 36.1, 56.0, 114.6, 115.0, 125.7, 137.0, 144.6, 145.5. MP: 143-146° C., MS m/z: 303, 287, 269, 240, 211, 195, 164, 145, 128, 105. EA Calcd. (found): C 71.50 (71.58), H7.33 (7.46).

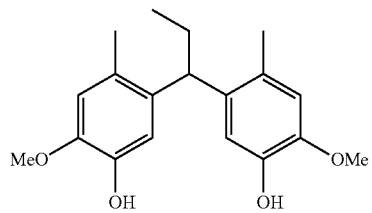

5,5'-(propane-1,1-diyl)bis(2-methoxy-4-methylphenol) (5)

5.02 g of 1 (36.4 mmol) and 1.04 g of propionaldehyde (17.9 mmol) were diluted in 10 mL of H$_2$O. 20 mL of 48% aqueous HBr was slowly added and the reaction was stirred at room temperature overnight. The supernatant was carefully decanted from the resultant oil and the product was washed with water. Work up by the standard method described above yielded 3.82 g of a viscous tan oil (67%). The product forms a solvent adduct with DMSO that crystallizes from ether solutions upon standing at room temperature. $^1$H NMR (d$_6$-DMSO) δ: 0.85 (t, 3H, J=7 Hz), 1.73 (t, 2H, J=7 Hz), 2.10 (s, 6H), 3.69 (s, 6H), 3.81 (t, 1 H, J=7 Hz), 6.52 (s, 2H), 6.65 (s, 2H), 8.55 (s, 2H). $^{13}$C NMR (d$_6$-DMSO) δ: 13.1, 18.9, 28.9, 43.3, 56.1, 114.9, 115.0, 126.3, 135.5, 144.5, 145.6. MS m/z: 316, 287, 257, 240, 211, 195, 167, 151, 131, 115. EA Calcd. (found) for 5·1.5H$_2$O: C 66.45(66.33), H7.92 (7.78).

Example—Cyanate Ester Synthesis from Renewable Bisphenols 3.54 mmol of a renewable bisphenol dissolved in 25 mL of diethyl ether was chilled to ~30° and 1.18 g (11.13 mmol) of CNBr was added. The solution was allowed to warm to 0° C. and was stirred at that temperature for one hour. The resulting off-white powder was collected on a frit and washed with ether and then water to yield a white solid that was subsequently dried in a vacuum oven.

Example—Polycarbonate Synthesis from Renewable Bisphenols 1 eq. of the starting bisphenol, 1.1 eq. of diphenyl carbonate and 2.5 mol% Zn(Ac)$_2$·2H$_2$O were added to a small round bottom flask. The flask was heated to 140° C. under N$_2$ for 2 hours, followed by 180° C. for 2 hours, and while maintaining the temperature, the flask was placed under reduced pressure (~30 torr) for an additional 2 hours. The pressure was then further reduced to ~1 torr and the temperature raised to 200° C. for 4 hours. The flask was cooled to room temperature and the solid dissolved in dichloromethane. Precipitation with hexanes yielded a white solid.

Example—Protection/Elimination of Phenols

Mesylation: 12.71 mmol of a renewable bisphenol was dissolved in 65 mL methylene chloride and 25.42 mmol of mesyl chloride was added followed by 25.42 mmol of triethylamine. The reaction mixture was stirred for three hours at room temperature. The solvent was removed under reduced pressure and the product was washed with distilled water and cold ethyl acetate to yield a white solid in 95% yield.

Triflation: A 30% K$_3$PO$_4$ solution (30 mL) was added to a stirred mixture of a bisphenol (1.74 mmol) in 30 mL of toluene. The reaction mixture was placed under a nitrogen atmosphere and chilled to 0° C. 5.23 mmol of triflic anhydride was added dropwise to the reaction mixture which was warmed to ambient temperature and stirred for 24 h. In a separatory funnel, the aqueous layer was discarded and the organic layer washed with distilled water. The toluene was then removed under reduced pressure to yield a white solid in 97% yield.

Elimination: 3.35 mmol Mg metal, 2.79 mmol ammonium acetate, and 0.0814 g of 10% Pd on carbon were added to a solution of 1.40 mmol of a protected (mesylate or triflate) bisphenol in 25 mL methanol. The mixture was stirred for five hours at room temperature and the solvent was then removed under reduced pressure. The residue was extracted with dichloromethane, filtered, and the organic layer washed with water. The organic layer was dried with MgSO$_4$ and the solvent removed to yield the product.

Example—Demethylation of Aryl Methoxy Compounds 1.37 mmol of a bis-aryl methoxy compound and 13.7 mmol of pyridine-HCl were heated to 180° C. under a nitrogen atmosphere for nine h. The resulting residue was dissolved in water and extracted with ethyl acetate. The ethyl acetate extracts were combined, washed with distilled water, dried with $MgSO_4$, and the solvent removed to yield the product.

Preparation of Renewable bis(cyanate) esters:

A series of renewable bis(cyanate) esters have been prepared from bisphenols synthesized by condensation of 2-methoxy-4-methylphenol (creosol) with formaldehyde, acetaldehyde, and propionaldehyde. The cyanate esters have been fully characterized by infrared spectroscopy. $^1H$ and $^{13}C$ NMR spectroscopy, and single crystal X-ray diffraction. These compounds melt from 88-143° C., while cured resins have glass transition temperatures from 219-248° C., water uptake (96 h, 85° C. immersion) in the range of 2.05-3.21%, and wet glass transition temperatures from 174-193° C. These properties suggest that creosol-derived cyanate esters may be useful to a wide variety of military and commercial applications. The cure chemistry of the cyanate esters has been studied with FTIR spectroscopy and differential scanning calorimetry. The results show that cyanate esters with more sterically demanding bridging groups cure more slowly, but also more completely than those with a bridging methylene group. In addition to the structural differences, the purity of the cyanate esters has a significant effect on both the cure chemistry and final $T_g$ of the materials. In some cases post-cure of the resins at 350° C. resulted in significant decomposition and off-gassing, but cure protocols that terminated at 250-300° C. generated void-free resin pucks without degradation.

Thermogravimetric analysis revealed that cured resins were stable up to 400° C. and then rapidly degraded. TGA/FTIR and mass spectrometry results showed that the resins decomposed to phenols, isocyanic acid, and secondary decomposition products including $CO_2$. Char yields of cured resins under $N_2$ ranged from 27-35%, while char yields in air ranged from 8-11%. These data suggest that resins of this type may potentially be recycled to parent phenols, creosol and other alkylated creosols by pyrolysis in the presence of excess water vapor. The ability to synthesize these high temperature resins from a phenol (creosol) that can be derived from lignin, coupled with the potential to recycle the composites, provides a possible route to the production of sustainable, high-performance thermosetting resins with reduced environmental impact.

Over the last several years there has been a renaissance of activity directed toward the development of full-performance polymeric materials derived from renewable feedstocks (Payne, G. F.; Smith, P. B., Eds. *Renewable and Sustainable Polymers ACS Symposium Series* 1063; American Chemical Society: Washington, D.C., 2011; pp 1-212; Williams, C. K.; Hillmyer, M. A. *Polym. Rev.* 2008, 48, 1-10; Stewart, D. *Ind. Crops Prod.* 2008, 27, 202-207). These efforts have paralleled similar thrusts in the realm of renewable fuels and chemicals (.Climent, M. J.; Corma, A.; Iborra, S. *Green Chem* 2011, 13, 520-540; Dinjus, E.; Arnold, U.; Dahmen, N.; Höfer, R.; Wach, W., in *Sustainable Solutions for Modern Economies*, ed. Höfer, R., RSC Publishing, Cambridge, 2009, ch. 8, pp. 125-163; Alonso, D. M.; Bond, J. Q.; Durnesic, J. A. *Green Chem.* 2010, 12, 1493-1513). Although the general paradigm is similar in that crude bio-feedstocks must first be deconstructed to tractable materials and then chemically converted to molecules with the required properties, the ultimate use of the products dictates the choice of feedstock as well as the methods used to upgrade the biomass. In the case of high temperature polymer systems, the most compelling renewable feedstock is lignin, based on cost, availability, and chemical structure. The long term cost of crude biomass is estimated at $60/dry ton, while the U.S. Department of Energy has predicted that up to 1.3 billion tons of biomass (~15-25% lignin) per year could be sustainably produced by 2030 (U.S. Department of Energy. 2011 *U.S. Billion-Ton Update: Biomass Supply for a Bioenergy and Bioproducts Industry*, R. D. Perlack and B. J. Stokes (Leads), ORNL/TM-2011/224. Oak Ridge National Laboratory, Oak Ridge, Tenn. 227p).

The aromatic structures present in lignin provide excellent high temperature stability combined with low reactivity, flammability, and hydrophilicity (Gandini, A. *Macromolecules* 2008, 41, 9491-9504), all important properties for high performance resins. In contrast to other abundant biopolymers such as cellulose or hemicellulose, lignin is not as attractive for the production of renewable fuels due to its complex structure and recalcitrance. In addition, aromatics do not burn as cleanly as linear or branched chain alkanes, and have relatively high melting points. Although methods have been developed to convert lignin to renewable fuels through processes such as pyrolysis, gasification, and hydroliquefication (U.S. Department of Energy. 2007. *Top Value-Added Chemicals from Biomass Volume II—Results of Screening for Potential Candidates from Biorefinery Lignin*. J. J. Bozell, J. E. Holladay, D. Johnson, and J. F. White, PNNL-16983. Pacific Northwest National Laboratory and the National Renewable Energy Laboratory; Jae, J.; Tompsett, G. A.; Lin, Y C., Carlson, T. R.; Shea, J.; Zhang, T.; Yang, B.; Wyman, C. E.; Conner, W. C.; Huber G. W. *Energy Environ. Sci.* 2010, 3, 358-365; Huber, G. W.; Iborra, S.; Corma, A. *Chem. Rev.* 2006, 106, 4044-4098), many of these transformations are hydrogen intensive and are perhaps less practical than other methods. Instead, within the concept of a biorefinery, a compelling case can be made for the production of fuels from the cellulosic and hemicellulosic components of biomass while utilizing the lignin as a source of aromatics, fine chemicals, and polymeric synthons such as phenols (.Zakzeski, J.; Bruijnincx, C. A.; Jongerius, A. L.; Wechhuysen, B. M. *Chem. Rev.* 2010, 110, 3552-3599. This parallel approach takes advantage of the chemical diversity of biomass and allows for the production of multiple product streams.

The use of lignin as a significant component of resins and composite formulations has a rich history. Lignin has been investigated as a precursor to low-cost carbon fiber (Kadla, J. F.; Kubo, S.; Venditta, R. A.; Gilbert, R. D.; Compere, A. L.; Griffith, W. *Carbon* 2002, 40, 2913-2920), a component of conducting polymers (Kuusela, T. A.; Lindberg, J. J.; Levon, K.; Osterholm, J. E. *ACS Symposium Series* 1989, 397, 219-227), and a macromonomer useful for the synthesis of polyesters (Guo, Z. X.; Gandini, A. *Eur. Polym. J.* 1991, 27, 1177-1180; Bonini, C.; D'Auria, M.; Emanuele, L.; Ferri R.; Pucciariello, R.; Sabia, A. R. *J. Appl. Polym. Sci.* 2005, 3, 1451-1456), polyurethanes (Thring, R. W.; Vanderlaan, M. N.; Griffin, S. L. *Biomass Bioenergy* 1997, 12, 125-132), and epoxy polymers (Hofmann, K.; Glasser, W. *Macromol. Chem. Phys.* 1994, 195, 65-80; Ismail, T. N.; Hassan, H. A.; Hirose, S.; Taguchi, Y.; Hatakeyama, T.; Hatakeyama, H. *Polym. Int.* 2010, 59, 181-186; Nonaka, Y.; Tomita, B.; Hatano, Y. *Holzforschung* 1997, 51, 183-187). Lignin has also been studied as a replacement for phenol-formaldehyde and urea-formaldehyde resins, sealants, and adhesives (Cetin, N. S.; Ozmen, N. *Int. J. Addhes. Addhes.* 2002, 22, 477-480). The most straightforward method for incorporating lignin into composites is as an oligomeric species. A disadvantage of this approach is the low degree of functionality per aromatic ring. Although a pure bisphenol has a hydroxyl/aromatic ring ratio of one, the ratio in Kraft lignin is approximately 0.5 (Li, S.; Lundquist, K. *Nord, Pulp Pap. Res. J.* 1994, 3, 191-195). This low degree of functionality results in a sparse 3-dimensional network upon cross-linking that is not expected to significantly increase the $T_g$ beyond that of the native lignin (roughly 150° C.) (El Mansouri, N. E.; Yuan, Q.; Huang, F. *Bioresources* 2011, 6, 2647-2662).

Scheme 5. Conversion of lignin to well-defined phenolics.

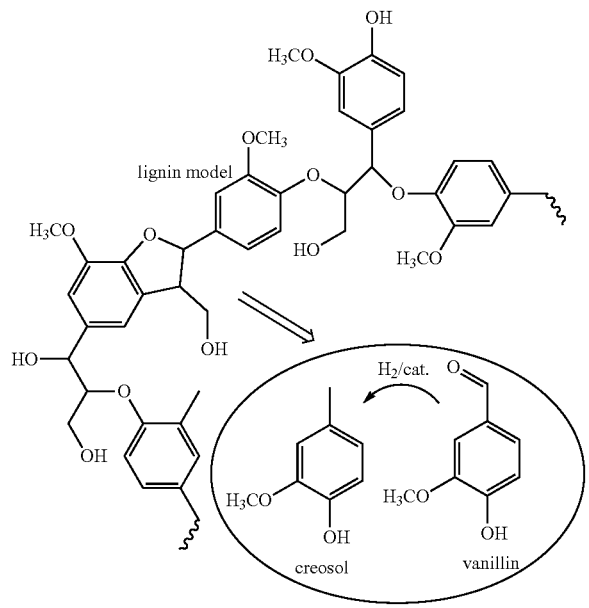

Although suitable for a variety commercial applications, this modest glass transition temperature greatly limits the use of lignin in high performance composite materials. In addition, the relatively high melting point of oligomeric lignin reduces the processability of resins and increases the difficulty of composite fabrication. Finally the complex heteroatom structures of the oligomers (Scheme 5) render them susceptible to hydrolysis and other cleavage reactions, diminishing the long term stability of composite materials based on lignin. The most straightforward way to circumvent these issues is to utilize pure or well-defined mixtures of phenols derived from lignin (Gandini, A. *Macromolecules* 2008, 41, 9491-9504). Among the candidate phenols, vanillin and 2-methoxy-4-methylphenol, or creosol, show a great deal of promise. Oxidation of lignin has been shown to yield up to ca. 14% vanillin (Pandey, M. P.; Kim, C. S. *Chem. Eng. Tech.* 2011, 34, 29-41) which has recently been studied as a precursor to both polyvanillin (Amarasekara, A. S.; Wiredu, V.; Razzaq, A. *Green Chem* 2012, 14, 2395-2397) and renewable vinyl esters (Stanzione, J. F.; Sadler, J. M.; La Scala, J. J.; Reno, K. H.; Wool, R. P. *Green Chem* 2012, 14, 2346-2352). Creosol can also be generated from lignin or is readily derived from vanillin through catalytic hydrogenation (Wang, Q.; Yang, Y.; Li, Y.; Yu, W.; Hou, Z. J. *Tetrahedron* 2006, 62, 6107-6112) (Scheme 5).

As described previously, efficient methods have been developed for the synthesis of bisphenols from creosol (Meylemans, H. A.; Groshens, T. J.; Harvey, B. G. *ChemSusChem* 2012, 5, 206-210). With the bisphenols in hand it became of interest to synthesize high temperature cyanate ester resins and to coduct some preliminary experiments to evaluate their suitability for a variety of applications. Cyanate ester resins have been studied extensively over the last several decades (Nair, C. P. R.; Dona, M.; Ninan, K. N. *Adv. Polym. Sci.* 2001, 155, 1-99; Hamerton, I.; Hay, J. N. *High Perform. Polym.* 1998, 10, 163-174; Snow, A. W.; Buckley, L. J. Cyanate ester resins with low dielectric properties and applications in *Handbook of Low and High Dielectric Constant Materials and Their Applications* ed. Nalwa, H. S. Academic Press San Diego, Calif. 1999 pp. 189-212) and are of interest due to a number of advantages over epoxy resins including high glass transition temperatures, low water uptake, and decreased flame, smoke, and toxicity (FST) for both monomers and cured resins. These properties make cyanate ester resins particularly interesting for use in marine and aerospace environments. Recently they have been used or proposed fur the fabrication of new high performance components including precision molded nanostructures (Gitsas, A.; Yameen, B.; Lazzara, T. D.; Steinhart, M.; Duran, H.; Knoll, W. *Nano Lett.* 2010, 10, 2173-2177), magnet casings for thermonuclear fusion reactors (Savary, F.; Bonito-Oliva, A.; Gallix, R.; Knaster, J.; Koizurri, N.; Mitchell, N.; Nakajima, H; Okuno, K.; Sborchia, C. *IEEE Trans. Appl. Supercond.* 2010, 20, 381-384), space telescopes (Chen, P. C.; Saha, T. T.; Smith, A. M.; Romeo, R. *Opt. Eng.* 1998, 37, 666-676), and interplanetary space probes (Wienhold, P. D.; Persons, D. F. *SAMPE J.* 2003, 39, 6-17). As an initial entry into the study of renewable cyanate esters, this paper discusses the synthesis, characterization, and cure chemistry of bis(cyanate) esters derived from creosol. These results are discussed within the context of conventional cyanate esters to evaluate both the benefits and limitations of the sustainable materials.

Experimental

General: The starting bisphenols were prepared as previously outlined. Cyanogen bromide and triethylamine were purchased from Sigma Aldrich and used as received. Anhydrous ether was obtained from Fischer Scientific and used as received. NMR spectra were collected on a Bruker Avance II 300 MHz NMR spectrometer. Samples of the cyanate esters were prepared in $CDCl_3$ and spectra were referenced to the solvent peaks ($\delta$=7.26 and 77.16 ppm $^1H$ and $^{13}C$ spectra, respectively). Fourier Transform Infrared Spectroscopy (FT-IR) was carried out using a Thermo Nicolet Nexuus 6700 FTIR equipped with the Smart iTr attenuated total internal reflection (ATR) accessory, single bounce diamond crystal. The detector type was a liquid nitrogen cooled MCTA. FTIR spectra are an average of 32 scans, at 4 $cm^{-1}$ resolution, and have been baseline and background corrected. Melting points were determined with a Mel-Temp apparatus; temperature values are uncorrected. Elemental analysis was performed by Atlantic Microlabs Inc. Norcross, Ga.

General Procedure for Synthesis of Cyanate Esters. Bisphenol (25 mmol) was dissolved in 100 mL of ether and cooled to −78° C. Cyanogen bromide (63 mmol) was added to the cooled mixture and allowed to dissolve. Triethylamine (50 mmol) was slowly added dropwise to the cooled mixture over the course of several minutes. The reaction was stirred at −78° C. for 30 min and then slowly warmed up to 0° C. and held at that temperature for the duration of the reaction. The reaction progress was monitored by TLC, and was complete in ~3 hours. The products were isolated as outlined below based on the solubility of the final product.

Bis(2-cyanato-3-methoxy-5-methylphenyl)methane (6). The reaction mixture was filtered and the residual solid washed with an excess of water to remove HNEt₃Br. Yield: 7.62 g (96%) of a white powder. The solid was further purified by dissolving in a minimum of ethyl acetate and then re-precipitating with ether. $^1$HNMR (CDCl₃) δ: 2.31 (s, 6H), 3.93 (s, 6H), 4.00 (s, 2H), 6.55 (s, 2H), 6.73 (s, 2H). $^{13}$CNMR (CDCl₃) δ: 21.48, 29.67, 56.29, 110.22, 112.64, 122.51, 129.86, 138.67, 138.80, 149.90. mp (powder): 143-146° C., (crystals): 156-158° C.; elemental analysis calcd. (%) C 67.44, H 5.36; found: C 67.17, H 5.46

Bis(5-cyanato-4-methoxy-2-methylphenyl)methane (7). This compound was isolated in an analogous manner to 6. Yield: 8.2 g (96% yield) of white solid. $^1$HNMR (CDCl₃) δ: 2.25 (s, 6H), 3.78 (s, 2H), 3.92 (s, 6H), 6.82 (s, 2H), 6.86 (s, 2H). $^{13}$CNMR (CDCl₃) δ: 19.47, 35.10, 56.30, 109.60, 115.53, 117.51, 130.21, 136.44, 140.28, 146.81. mp: 122-124° C.; elemental analysis calcd. (%) C 67.44, H 5.36; found: C 67.50, H 5.36.

5,5'-(ethane-1,1-diyl)bis(1-cyanato-2-methoxy-4-methylbenzene) (8). Volatiles were removed under reduced pressure and the resulting solid was dissolved in ethyl acetate. The organic layer was washed three times with water and dried over MgSO₄. Most of the solvent was removed under reduced pressure and then a small amount of ether was added. The mixture was placed at −15° C. to crystallize. 7.93 g (88%) of a white microcrystalline material was obtained. $^1$HNMR (CDCl₃) δ: 1.48 (d, 3H, J=7 Hz), 2.20 (s, 6H), 3.89 (s, 6H), 4.22 (d, 1H, J=7 Hz), 6.80 (s, 2H), 6.98 (s, 2H). $^{13}$CNMR (CDCl₃) δ: 19.15, 20.75, 36.71, 56.25, 109.74, 115.52, 115.69, 135.80, 136.24, 140.34, 146.61. mp: 87-88° C.; elemental analysis calcd. (%) C 68.17, H 5.72; found: C 68.24, H 5.78.

5,5'-(propane-1,1-diyl)bis(1-cyanato-2-methoxy-4-methylbenzene) (9). This compound was prepared in an analogous manner to 3. Yield: 4.25 g (46%). $^1$ NMR (CDCl₃) δ: 0.92 (t, 3H, J=7 Hz), 1.89 (q, 2H, J=7 Hz), 2.24 (s, 6H), 3.90 (s, 6H), 3.98 (t, 1H, J=7 Hz), 6.79 (s, 2H), 7.01 (s, 2H). $^{13}$CNMR (CDCl₃) δ: 12.56, 19.44, 28.68, 43.66, 56.22, 109.75, 115.63, 115.97, 134.88, 136.28, 140.38, 146.54. mp: 115-117° C.; elemental analysis calcd. (%) C 68.84, H 6.05; found: C 68.85, H 6.02.

X-ray Diffraction Studies. X-ray intensity data were collected for omega scans at 296K on a Bruker SMART APEX II diffractometer with graphite-monochromated Mo Kα radiation (λ=0.71073Å). Frames were integrated using the Bruker SAINT software package with a narrow-frame integration algorithm. Data were corrected for absorption using the empirical multi-scan method (SADABS), and the structures solved by direct methods using SHELXTL and refined by full-matrix least squares refinement on F². X-ray data for compounds 6-9 have been deposited in the Cambridge Structual Database (CCDC 888614 (2), 888615 (3), and 888616 (4) contain the supplementary crystallographic data for this paper. These data can be obtained free of charge from The Cambridge Crystallographic Data Centre through www.ccdc.cam.ac.uk/data request/cif).

TGA/FTIR Analyis. Samples were analyzed using a Thermo Nicolet Nexuus 6700 FTIR interfaced via a heated gas cell and transfer line (held at 150° C.) to a TA instruments Q50 TGA. The FTIR detector type was a liquid nitrogen cooled MCTA. FTIR spectra are an average of 16 scans, at 4 cm$^{-1}$ resolution, and have been baseline and background corrected. The TGA was set to ramp from room temperature to 400 degrees Celsius at a rate of 10 degrees per minute.

Preparation of Resin Pucks. Cured polycyanurate samples were prepared by heating the cyanate ester in a 6 mL glass vial to a temperature just above the melting point of the monomer. Once in the liquid state, the material was degassed at 300 mm Hg for 30 minutes and then poured into silicone molds made from R2364A silicone from Silpak Inc. (mixed at 10:1 by weight with R2364B platinum-based curing agent, degassed for 60 minutes at 25° C. and cured overnight at room temperature, followed by post-cure at 150° C. for 1 hour). The open mold and sample were then placed in an oven at 25° C. under flowing nitrogen and cured following a cure protocol of 150° C. for 1 hour and 210° C. for 24 hours using a ramp rate of 5° C./min except for 1 which was cured at 170° C. for 1 hour and 210° C. for 24 hours. Void-free, transparent yellow-orange vitreous discs with smooth surfaces and no evidence of shrinkage, bubbles, or phase separation, measuring approximately 11.5-13.5 mm in diameter by 1-3 mm thick and weighing 200-400 mg were obtained by this method. The discs were used for thermomechanical analysis (TMA) and hot water exposure tests.

Thermoset Characterization. DSC was performed on a TA instruments Q200 calorimeter under 50 mL/min. of flowing nitrogen. Samples were subjected to a heat-cool-heat cycle from 40° C. to 350° C. with a ramp rate of 10° C./min. Oscillatory TMA was conducted with a TA instruments Q400 series analyzer under 50 mL/min of nitrogen flow. The discs were held in place via a 0.2 N initial compressive force with the standard ~5 mm diameter flat cylindrical probe while the probe farce was modulated at 0.05 Hz over an amplitude of 0.1 N (with a mean compressive force of 0.1 N). The polycyanurate samples were subjected to two heating cycles and a cycle to determine thermal lag (A detailed explanation of thermal lag may be found in Guenthner, A. J.; Yandek, G. R.; Mabry, J., M; Lamison, K. R.; Vij, V.; Davis, M. C.; Cambrea, L. R., Insights into moisture uptake and processability from new cyanate ester monomer and blend studies. in *SAMPE International Technical Conference*, SAMPE International Business Office: Salt Lake City, Utah, 2010; Vol. 55, pp 42ISTC-119). For samples not exposed to water, samples were cycled twice between −50 and 200° C. at 50° C./min to determine thermal lag with the exception of 6 which was cycled between −70 and 170° C. To determine $T_g$ for 7,8 and 9 the temperature was then ramped to 300° C., cooled to 100° C. and ramped again to 380° C., all at 50° C./min. 6 was ramped to 250° C., cooled to 100° C. and ramped again to 300° C., at 50° C./min. Discs that were exposed to water were ramped from 40° C. to 350° C., cycled between 100° C. and 200° C. to determine thermal lag and ramped again to 350° C./min, all at 20° C./min. Density of the cured samples was determined using solutions of calcium chloride in deionized water. Discs of the partially cured polycyanurates were placed in a vessel and two solutions, at different concentrations, were combined until a neutrally buoyant solution was obtained. The density of the neutral solution was measured by weighing a 10 mL aliquot of the solution using a volumetric flask. This value was compared to the expected density of a calcium chloride solution at the known concentration and ambient conditions. Thermogravimetric analysis (TGA) (without FT-IR) was performed on a TA Instruments Q5000 analyzer with either nitrogen or air flow of 25 mL/min. The samples were heated from ambient to 600° C. at 10° C./min. Moisture uptake experiments were performed using cured discs of uniform 11.7 mm diameter and 3 mm thickness. Each disk was placed into ~300 mL of deionized water maintained at a temperature of 85° C. for 96 hours. The discs were then removed from the water, gently patted dry with a paper towel, and weighed a minimum of three times (all weights agreed to within 0.0005 g) and then tested via oscillatory TMA to measure "wet" glass transition temperatures.

Mass Spectrometry. Mass spectra of cured resin pucks were obtained by the Direct Insertion Probe method (DIP-MS) using a ThermoFisher DSQII. A small amount of sample was placed in a quartz-micro tube, and inserted into the MS chamber (~20 mTorr) using a direct insertion probe. During analysis the probe was maintained at 30° C. for 30 seconds, and the temperature was then increased to 450° C. at 10° C./min, and held at 450° C. for five minutes. Mass data were collected for the duration of the temperature program.

Synthesis of bis(cyanate) esters. The cyanate esters were readily isolated in good to excellent yields by allowing the bisphenols to react with cyanogen bromide and triethylamine at low temperature (Scheme 2). Diethyl ether was selected as a solvent and in the case of 6 and 7, the product cyanate esters precipitated in addition to HNEt3Br.

These solids were readily purified by a water wash followed by recrystallization. In contrast, 8 and 9 with their additional aliphatic carbons maintained a significant amount of solubility in ether, but could be obtained in excellent purity by washing ethyl acetate solutions of the cyanate esters with water followed by crystallization from ether/ethyl acetate solutions. Compounds 6-8 were isolated in nearly quantitative yields, whereas 9, with its greater solubility in ether, was isolated in 46% yield.

Characterization of bis(cyanate) esters. Compounds 6-9 were characterized by $^1$H and $^{13}$C NMR spectroscopy, attenuated total reflectance Fourier transform infrared spectroscopy (ATR-FTIR), elemental analysis, and with the exception of compound 6, single crystal X-ray diffraction. NMR spectroscopic analysis of compounds 7 and 8 revealed a trace of the cyanate esters with one of the ring bridging through the position ortho to the cyanate ester group. This

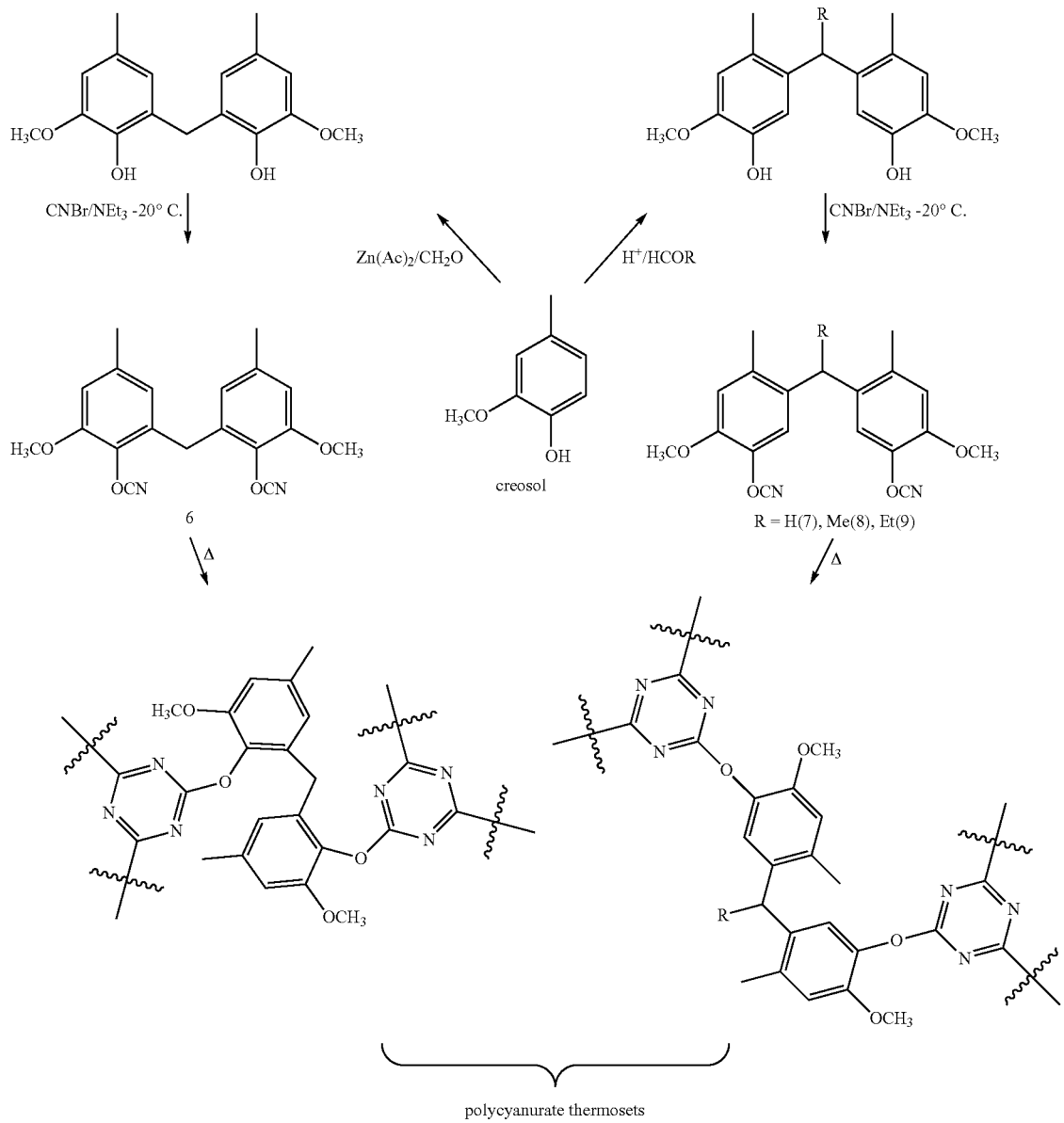

Figure 4:
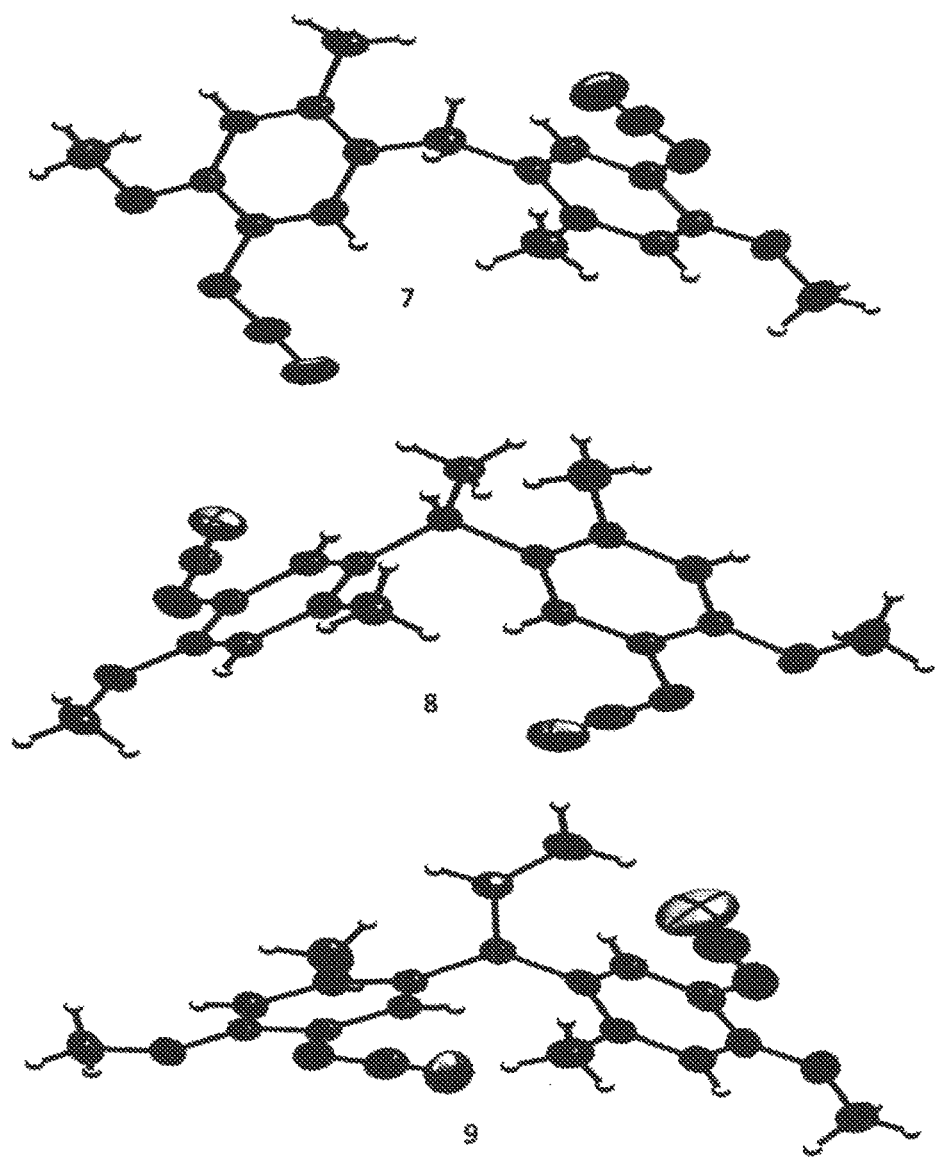
FIG. 4 are perspective views of the solid state structures of compounds 7-9according to embodiments of the invention.

Scheme 6. Synthesis of bis(cyanate)esters and polycyanurate thermosets from creosol.

was predicted based on the starting phenols, but these trace isomers are expected to have only a minor impact on the melting point, cure kinetics, and physical properties of the resins. The IR spectra for 7-9 (FIG. 4) contained two overlapping CN stretching bands due to asymmetric environments for the cyanate ester functionalities in the solid state. In contrast, 6 exhibited only a single broad cyanate ester peak, suggesting that both cyanate ester groups are in similar environments; this result is in line with the solid state structure of the parent phenol. In addition to IR data, these compounds have been thoroughly characterized by NMR spectroscopy and other analytical techniques (Meylemans, H. A.; Harvey, B. G.; Reams, J. T.; Guenthner, A. J.; Cambrea L. R.; Groshens, T. J.; Baldwin, L. C.; Garrison, M. D.; Mabry, J. M. *Biomacromolecules* 2013, 14, 771-780)

The X-ray structures of the cyanate esters are significantly affected by the aliphatic groups on the bridging carbon atom. In the case of 7, the cyanate esters are nearly diametrically opposed with a torsional angle between —CN groups of 157°. This configuration also results in an intermolecular N—N distance of 8.292(3) Å. In contrast, the methyl group in 8 results in rotation of the aromatic rings and reduces the torsional angle to 96° with an N—N distance of 6.745(3) Å. The ethyl group in 9 exerts even more influence on the structure and although the torsional angle (97°) is similar to that of 8, the N—N distance is significantly reduced to 5.139(4) Å.

TABLE 3

Melting Points of Cyanate Esters and Parent Phenols

| Compound | $T_m$ (standard) | $T_m$ (DSC) | Phenol $T_m$ |
|---|---|---|---|
| 1 | 143-146 | 150.7 | 123-125 |
| 2 | 122-124 | 125.4 | 131-134 |
| 3 | 87-88 | 90.8 | 143-146 |
| 4 | 115-117 | 119.6 | Liquid at RT |

The solid state structures of cyanate esters impart physical properties to the solids that can have important implications for the utility of these materials. Crystalline materials with lower melting points allow for more straightforward fabrication processes that require less energy input. Additionally, for materials that melt at <100° C., hot water can be used as the heat source to generate molten resins. Although the solid state structures of 8 and 9 are quite similar, the melting points are significantly different with 8 having a melting point almost 30 degrees lower than 9 (Table 3). This is similar to the difference in melting point between the conventional cyanate esters LeCy and BADCy (chemical structures below), with LECy existing as a supercooled liquid at room temperature (mp=29° C.) and BADCy having a melting point of 79° C. The presence of an unsubstituted methylene linkage, as in 4,4'-dicyanatodiphenylmethane, yields a resin with an even higher melting point (108° C.) (Cambrea, L. R.; Davis, M. C.; Groshens, T. J.; Guenthner, A. J.; Lamison, K. R.; Mabry, J. M. *J. Polym. Sci. Part A* 2010, 48 4547-4554).

The melting point trend for the conventional cyanate esters can be explained in terms of a molecular symmetry argument (Brown, R. J. C.; Brown, R. F. C. *J. Chem. Ed.* 2000, 77, 724-731), but for 1-4, such an argument is not complete. Compound 6, which is isolated from a symmetric bisphenol precursor and has been shown to be symmetric in the solid state by IR, has the highest melting point. This is followed by 7 which also has a methylene linkage. Introducing a methyl group at the bridging carbon disrupts the symmetry of the molecule and as expected, results in a lower melting point. However, introduction of an ethyl group, as in 9, results in a surprising increase in melting point of nearly 30° C. Some insight into this trend can be obtained from a comparison of the space groups of these cyanate esters (Table 4). Compound 9 crystallizes in the monoclinic P 1 21/c 1 space group (Table 4), whereas 8 crystallizes in the triclinic P-1 space group. The higher degree of symmetry inherent to the monoclinic space group provides a possible explanation for the higher melting point of 9. Compound 7 also crystallizes in a monoclinic space group (C 1 2/c 1) and the similarity between the melting points of 7 and 9 suggests that space group symmetry may be more important for influencing the melting point than the subtle differences between hydrogen, methyl, and ethyl groups on the bridging carbon.

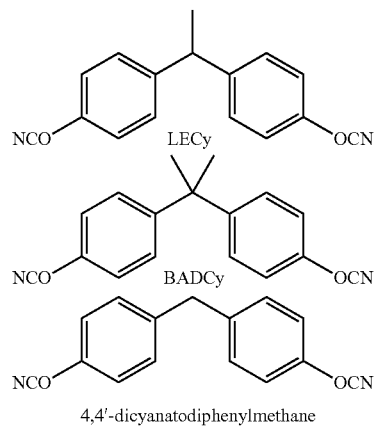

4,4'-dicyanatodiphenylmethane

Structures of Conventional Cyanate Esters

Interestingly, the melting point of the cyanate esters shows a different trend compared to the phenols, with the parent phenol of 8 having the highest melting point. However in the case of the phenols, other effects such as hydrogen bonding play important roles in crystal packing. Also of note, in the case of 6, the cyanate ester has a significantly higher melting point than the parent phenol. Due to the lank of hydrogen bonding in the bis(cyanate) ester, one on expect the opposite result. Unfortunately, we were unable to isolate X-ray quality crystals of 6 that would allow for comparative study of the solid state structure of 6 with the corresponding phenol.

TABLE 4

X-ray Crystallographic Data for Cyanate Esters 7-9

| Property | Compound 7 | Compound 8 | Compound 9 |
|---|---|---|---|
| Empirical formula | $C_{19}H_{18}N_2O_4$ | $C_{20}H_{20}N_2O_4$ | $C_{21}H_{22}N_2O_4$ |
| Formula weight | 338.35 | 352.38 | 366.41 |

TABLE 4-continued

X-ray Crystallographic Data for Cyanate Esters 7-9

| Property | Compound 7 | Compound 8 | Compound 9 |
|---|---|---|---|
| Crystal system | monoclinic | triclinic | monoclinic |
| Space group | C 1 2/c 1 | P −1 | P 1 21/c 1 |
| Unit cell dimensions | a = 17.5687(12) Å | a = 7.062(2) Å | a = 9.0462(6) Å |
| | α = 90° | α = 106.625(4)° | α = 90° |
| | b = 4.7770(3) Å | b = 11.734(4) Å | b = 15.0946(10) Å |
| | β = 112.4460(10)° | β = 95.476(4)° | β = 102.9660(10)° |
| | c = 22.8294(16) Å | c = 12.337(4) Å | c = 14.9988(10) Å |
| | γ = 90° | γ = 105.337(2)° | γ = 90° |
| Volume | 1770.8(2) Å$^3$ | 928.4(5) Å$^3$ | 1995.8(2) Å$^3$ |
| Z | 4 | 2 | 4 |
| Density (calculated) | 1.269 g/cm$^3$ | 1.261 g/cm$^3$ | 1.219 g/cm$^3$ |
| Crystal size (mm) | 0.075 × 0.182 × 0.212 | 0.092 × 0.205 × 0.433 | 0.148 × 0.179 × 0.340 |
| Theta(max) | 24.99° | 25.00° | 25.00 |
| Reflections collected | 9088 | 10119 | 21371 |
| Reflections 'observed' | 953 [I>2σ(I)] | 2291 [I>2σ(I)] | 2693 [I>2σ(I)] |
| Independent reflections | 1563 [R(int) = 0.0430] | 3281 [R(int) = 0.0245] | 3504 [R(int) = 0.0253] |
| Data/restraints/parameters | 1563/0/127 | 3281/0/256 | 3504/0/270 |
| Goodness-of-fit on F$^2$ | 1.011 | 1.023 | 1.038 |
| Final R indices [I>2sigma(I)] | R1 = 0.0415 wR2 = 0.0917 | R1 = 0.0404 wR2 = 0.0961 | R1 = 0.0397 wR2 = 0.1005 |

Cure Chemistry

Initial insight into the cure chemistry of these resins was obtained from DSC measurements. Compound 6 melted in the DSC at over 150° C. and exhibited a broad and immediate exotherm upon melting that culminated in a peak cure exotherm at 226° C. Compound 7, which melted at ~120° C. exhibited a stable processing window, but a relatively low cure exotherm at 216° C. The enthalpy change for the cure was 211 kJ/mol or 106 kJ/mol(cyanate ester) which compares favorably to the widely accepted value of 100 kJ/mol. Compound 8 is the lowest melting resin of the four compounds and displays a cure exotherm maximum at 283° C. with a cure enthalpy of 104 kJ/mol(cyanate ester). Similarly, compound 9 has a cure exotherm maximum at 285° C. and a cure enthalpy of 99 kJ/mol(cyanate ester). Overall, this data suggests that 6-9 approach complete cure under the DSC conditions. Further evidence of the degree of cure can be extracted from a comparison of the IR spectra of uncured cyanate esters and fully cured thermosets. This data can be found in the following reference and supporting information: Meylemans, H. A.; Harvey, B. G.; Reams, J. T.; Guenthner A. J.; Cambrea, L. R.; Groshens, T. J.; Baldwin, L. C.; Garrison, M. D.; Mabry, J. M. *Biomacromolecules* 2013, 14, 771-780. The IR traces show virtually quantitative conversion of the cyanate esters to cyanurate rings for all of the resins. The DSC and infrared spectroscopy results, which are summarized in Table 4, suggest that 8 and 9 are the most promising cyanate esters on the basis of an acceptable processing window and high degree of cure.

Figure 5:
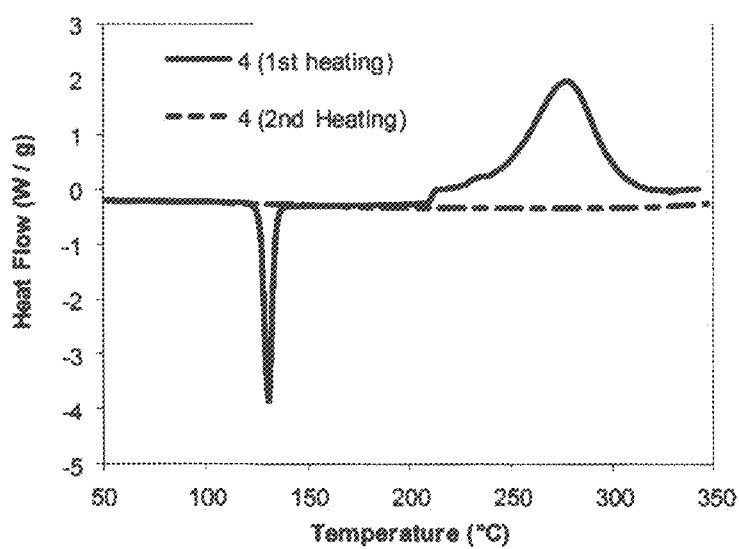
FIG. 5 is a graph showing the DSC curve for compound 9, according to embodiments of the invention.

FIG. 5. DSC curve for Compound 4.

Figure 6:
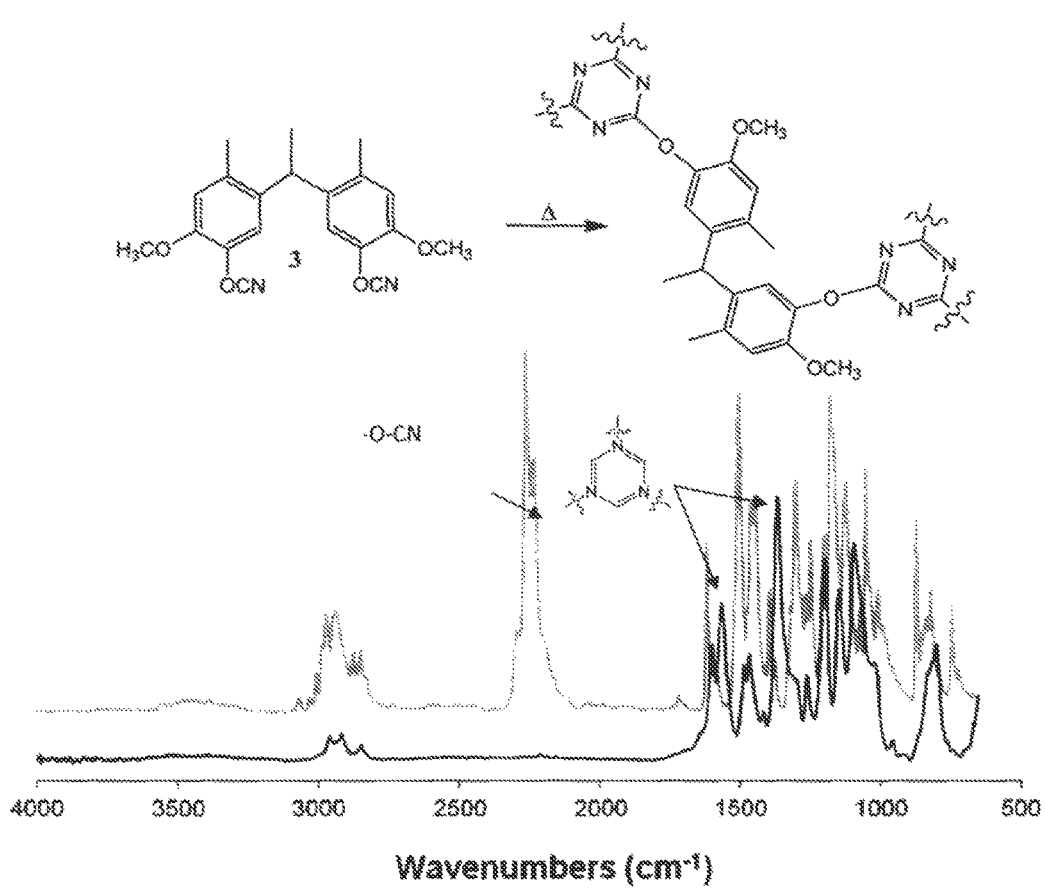
FIG. 6 is a graph showing a conversion of compound 8 to a polycyanurate network. The IR spectrum of 8 is shown having cure conditions: 150° C., 1 h, 210° C., 24 h, according to embodiments of the invention.

FIG. 6. Conversion of compound 3 to a polycyanurate network. The IR spectrum of 3 is shown in red and fully cured resin in blue. Cure conditions: 150° C., 1 h, 210° C., 24 h

TABLE 5

Summary of DSC data for renewable cyanate esters

| | Compound | | | |
|---|---|---|---|---|
| | 6 | 7 | 8 | 9 |
| Processing Window (° C.) | — | ~20 | ~120 | ~60 |
| Cure Exotherm (max, ° C.) | 226 | 216 | 283 | 285 |
| Cure Enthalpy (kj/mol-OCN) | 59 | 106 | 104 | 99 |
| Degree of Cure | <60% | Complete | Complete | Complete |

To measure the glass transition temperatures of the cured resins, pucks were subjected to TMA analysis. Based on the DSC data it was expected that 6 would not fully cure, leading to a modest glass transition temperature. Indeed this was the case with an as cured Tg of 181° C. Further heating to 350° C. actually decreased the Tg to 178° C., likely due to decomposition reactions at the elevated temperature. TGA experiments confirmed that 6 experienced significant weight loss at that temperature. The as-cured Tg's for the meta-substituted cyanate esters were all essentially the same at 257° C., while the fully cured Tg's ranged from 214-248° C. for compounds 7-9, respectively (Table 6). Again, the cause of this decrease in Tg was attributed to decomposition reactions. 7 is anomalous among these resins, as it's Tg only drops 9 degrees upon heating at the elevated temperature, whereas 8 and 9 both have their Tg drop 43 degrees. This result is consistent with the observation that pucks formed from 8 and 9 were subject to foaming upon heating to 350° C. This provided visual evidence that the thermosets had undergone decomposition that resulted in significant outgassing. In contrast, the puck prepared from 7 was intact. The more subtle decrease in $T_g$ for compound 7 is likely attributable to decomposition reactions on a more modest scale.

In addition to the dry $T_g$, it was of interest to evaluate the performance of these thermosets in wet conditions (Table 7). To determine a wet $T_g$, resin pucks were immersed in 85° C. water for 96 h and then analyzed by TMA. The lowest water uptake was observed for 6 and 7, while 9 had the highest water uptake. One possible explanation for this behavior is that 8 and 9 cure more completely than 7. The as cured $T_g$ is quite similar for 7-9 even though 8 and 9 would be expected to have lower $T_g$'s based on their intrinsically more flexible structures. This higher degree of cure then leads to the formation of more void space which increases the uptake of water molecules. Consistent with this hypothesis, the higher uptake of water molecules leads to a greater extent of network hydrolysis, and thus lower "wet" $T_g$ values for 8 and 9. As an explanation for the similarity of the dry and wet $T_g$'s exhibited by 6, it has previously been observed (Guenthner, A. J.; Yandek, G. R.; Mabry, J., M; Lamison, K. R.; Vij, V.; Davis, M. C.; Cambrea, L. R., Insights into moisture uptake and processability from new cyanate ester monomer and blend studies in *SAMPE International Technical Conference*, SAMPE International Business Office: Salt Lake City, Utah, 2010; Vol. 55, pp 42ISTC-119) that cyanurate networks with lower cross-linking densities tend to show "wet" $T_g$ values very close to the dry $T_g$ values, apparently because exposure to water results in simultaneous trimerization of unreacted cyanate esters and network hydrolysis.

TABLE 6

Key properties of cyanate ester resins (high temperature cure)

| | Compound | | | |
|---|---|---|---|---|
| | 6 | 7 | 8 | 9 |
| Density (g/cc) | 1.237 | 1.223 | 1.198 | 1.190 |
| Cyanurate Density[a] (mmol/cc) | 2.59 | 2.56 | 2.41 | 2.29 |
| As Cured $T_g$ (LP[b], ° C.) | 172 | 255 | 253 | 254 |
| As Cured $T_g$ (tan δ, ° C.) | 181 | 257 | 257 | 257 |
| Fully Cured $T_g$ (LP[b], ° C.) | 166 | 243 | 196 | 198 |
| Fully Cured $T_g$ (tan δ, ° C.) | 178 | 248 | 214 | 214 |

[a]For the fully cured samples.
[b]LP stands for Loss Profile.

TABLE 7

Wet Glass Transition Temperatures and Water Uptake of Resins

| Compound | Wet $T_g$ (tan δ, ° C.) | Water uptake (%) |
|---|---|---|
| 6 | 174 | 2.05 |
| 7 | 193 | 2.05 |
| 8 | 185 | 2.61 |
| 9 | 161 | 3.21 |

To minimize any decomposition reactions while allowing the resins to approach complete cure, a new series of pucks were prepared and post-cured in the TMA at 250° C. (for 6) and 300° C. for 7-9. These low-temperature conditions resulted in fully $T_g$'s comparable to the as-cured $T_g$'s while maintaining the integrity of the pucks. In contrast to the high temperature method, 6 cured completely under these conditions and all of the resins had similar $T_g$'s (231-248° C.) with the exception of 8 which had a $T_g$ of only 219° C. (Table 8). The lower $T_g$ observed for 8 suggests that it does not achieve complete cure under these conditions. Also of interest, the puck made from 9 showed significant degradation and some off-gassing when heated to 350° C. To determine whether this was due to impurities, a sample of 9 was purified by flash chromatography on silica gel and a puck was fabricated. The "high purity" puck had a $T_g$ 13 degrees higher and was stable at 350° C. This result highlights the fact that the purity of the cyanate esters can have a profound impact on the properties of the resulting cured resins.

TABLE 8

Glass Transition Temperatures of Cured Resins (Low Temperature Post-Cure)

| Compound | $T_g$(LP[a], ° C.) | $T_g$(tan δ, ° C.) |
|---|---|---|
| 1 | 236 | 238 |
| 2 | 240 | 248 |
| 3 | 206 | 219 |
| 4 | 219 | 231 |
| 4[b] | 238 | 244 |

[a]LP = loss profile.
[b]Purified by flash chromatography

Figure 7:
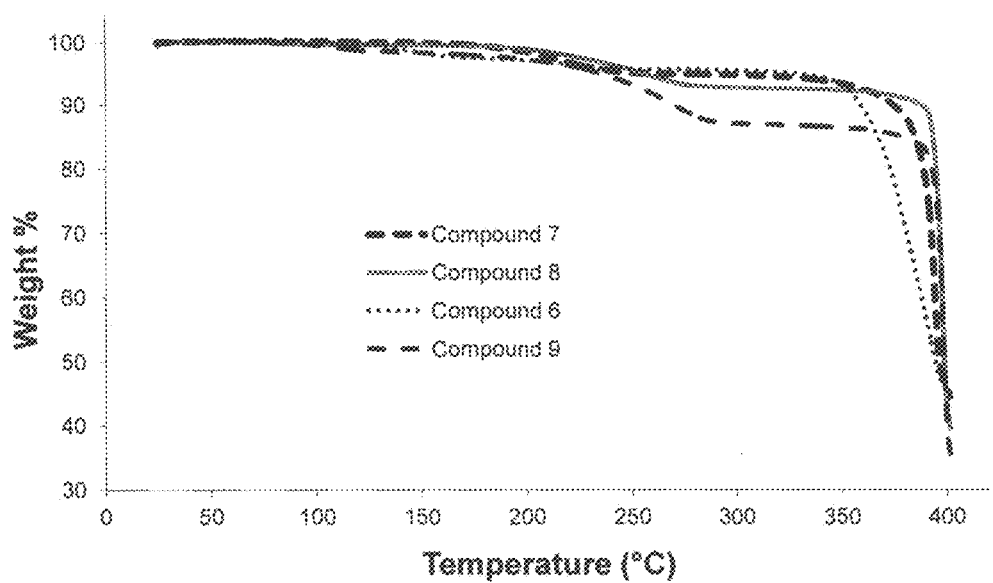
FIG. 7 is a graph showing TGA ($N_2$) of compounds 6-9, according to embodiments of the invention.

To further evaluate the cure chemistry of the cyanate esters, TGA/FTIR data were collected on uncured samples that were heated from ambient temperature up to 400° C. under a nitrogen atmosphere. Gas phase spectra of pyrolysis products were collected with an in-line spectrometer. Compound 6 was stable up to ~350° C. and then rapidly degraded, losing 56% of its mass by 400° C. (FIG. 5). In contrast, compounds 7-9 showed significantly different behavior than 6 and these results provided insight into both the cure chemistry and decomposition mechanisms for these resins. 7 exhibited a weight loss of ca. 5% between 180 and 250° C. After this initial weight loss, the material maintained a consistent weight up to 350° C. followed by an additional weight (FIG. 7. TGA ($N_2$) of Compounds 1-4) loss of 7% up to 380° C. and rapid weight loss above this temperature to give 55% weight loss by 400° C. Compound 8 had a weight loss of 7% between 210 and 280° C., but unlike 7, compound 8 was stable up to 390° C. and then rapidly degraded. Compound 9 had the highest low temperature weight loss of all the resins (10% between 200 and 290° C.) and had similar thermal stability to 8 with decomposition occurring at 390° C.

The gas phase FTIR data of volatile decomposition products collected at low temperature (~200-290° C.) for compounds 7-9 are consistent with evolution of isocyanic acid and suggest that decomposition of a partially reacted polycyanurate network occurs via an unreacted —OCN group which is then converted to a carbamate followed by decomposition to yield $_a$ phenol and isocyanic acid (Scheme 7) (Hamerton, I.; Emsley, A. M.; Howlin, B. J.; Klewpatinond, P.; Takeda, S. *Polymer* 2004, 45, 2193-2199; Kasehagen, L. J.; Haury, I.; Macosko, C. W.; Shimp, D. A. *J. Appl. Polym. Sci.* 1996, 64, 107-118). The progressive increase in low temperature weight loss from 7-9 suggests that the molecules with alkyl groups on the bridging carbon atom cure slower than 7. This result is consistent with the greater steric crowding in these molecules which allow for incomplete networks to exist for longer times at elevated temperatures, resulting in decomposition of unreacted cyanate ester functionalities. Despite this correlation, other factors, particularly the purity of the respective cyanate ester resins may also play a significant role in the rate of cure. Although all of the resins utilized in this work were shown to be pure by conventional analytical techniques, in other cyanate ester studies, trace impurities (even those around 0.1%) have been shown to have a significant effect on the cure rate (Guenthner, A. J.; Davis, M. C.; Lamison, K. R.; Yandek, G. R.; Cambrea, L. R.; Groshens, T. J.; Baldwin, L. C.; Mabry, J. M. *Polymer* 2011, 52, 3933-3942 and references contained therein). In spite of their propensity to cure slower, compounds 8 and 9 appear to cure more completely, allowing them to have roughly the same Tg as 7, despite the greater flexibility of the native resins. This higher degree of cure also imparts greater thermal stability to the network polymers formed from 8 and 9, as shown by the delayed onset of high temperature degradation observed from the TGA studies.

Scheme 7. Low temperature decomposition pathway for incompletely formed tricyanurate networks.

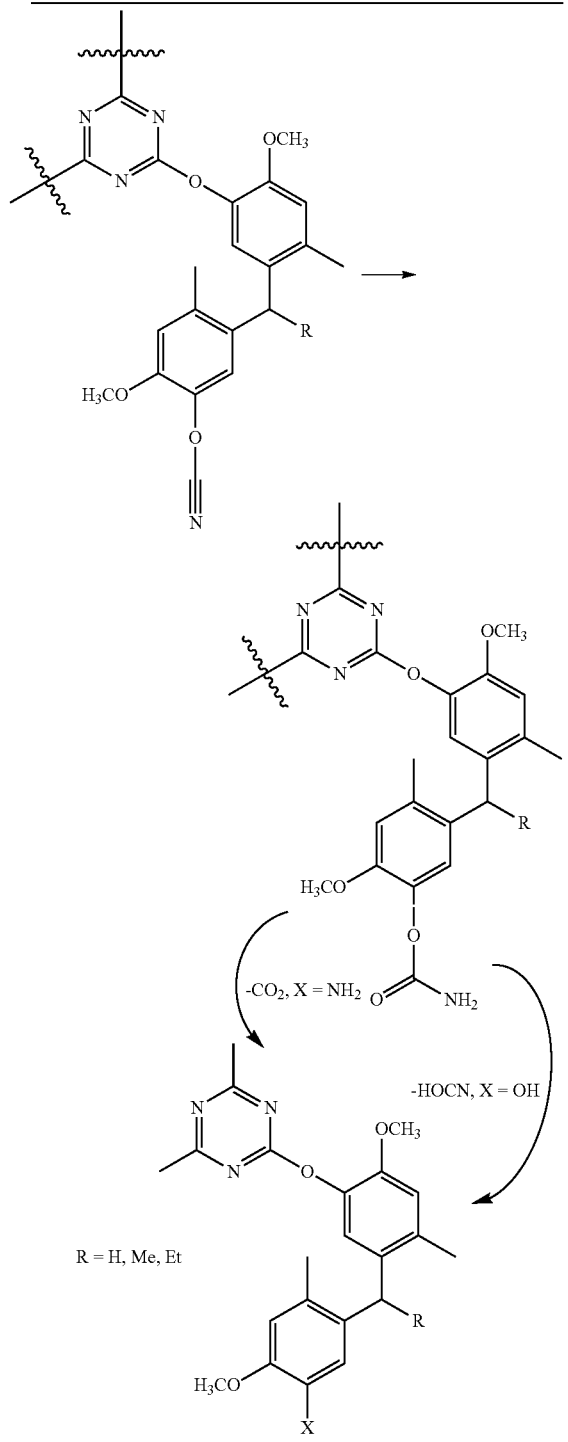

R = H, Me, Et

For all of the cyanate esters, gas phase FTIR data of the pyrolysis products at 390-400° C. showed evolution of isocyanic acid, methane, and phenolic compounds. The phenols are characterized by a distinctive O—H stretch at 3550 cm$^{-1}$ as well as two overlapping summation bands at ~1850 cm$^{-1}$. Initially we believed that the primary decomposition products were bisphenols, however, taking compound 8 as an example, comparison to the IR spectrum of the parent bisphenol with the gas phase spectrum of the pyrolysis products (FIG. 8) showed that in addition to the bisphenol, the evidence points to cleavage of the bridging group between aromatic rings. Although there is relatively good overlap of the IR bands below ~1620 cm$^{31\ 1}$, the bands at 1850 cm$^{-1}$ are particularly diagnostic and match well with the reported spectrum for creosol (IR spectral data can be obtained at the following web address: http://riodb01.ibase.aist.go.jp/sdbs/cgi-bin/cre_index.cgi?lang=eng). To further characterize the decomposition products, we analyzed cured resin samples in a mass spectrometer. Taking compound 8 as an example, the temperature was ramped from ambient temperature up to 450° C. at 10° C./min. Similar to the IR results, onset of decomposition (under vacuum) was observed at 375° C. and no volatiles were observed above 440° C. Although modest peaks were observed for the molecular ion at m/z=302 and loss of a methylene group at m/z=288, the peak with the highest intensity in the mass spectrum had m/z=138 which corresponds with creosol. Another significant peak was observed at m/z=152 which corresponds to a methyl creosol fragment, ostensibly derived from cleavage of the ethylidene bridging group (Scheme 8). Similarly, the molecular ion peaks of the bisphenols were observed for compounds 6, 7, and 9 in their respective spectra, along with cleavage products primarily comprised of alkylated creosols. On the basis of the mass spectrometry results and gas phase IR data, it is clear that the primary decomposition products are the parent phenols along with phenolic fragments generated by cleavage of the aliphatic bridging groups between aromatic rings. The residual cyanurate rings decompose primarily to isocyanic acid.

Figure 8:
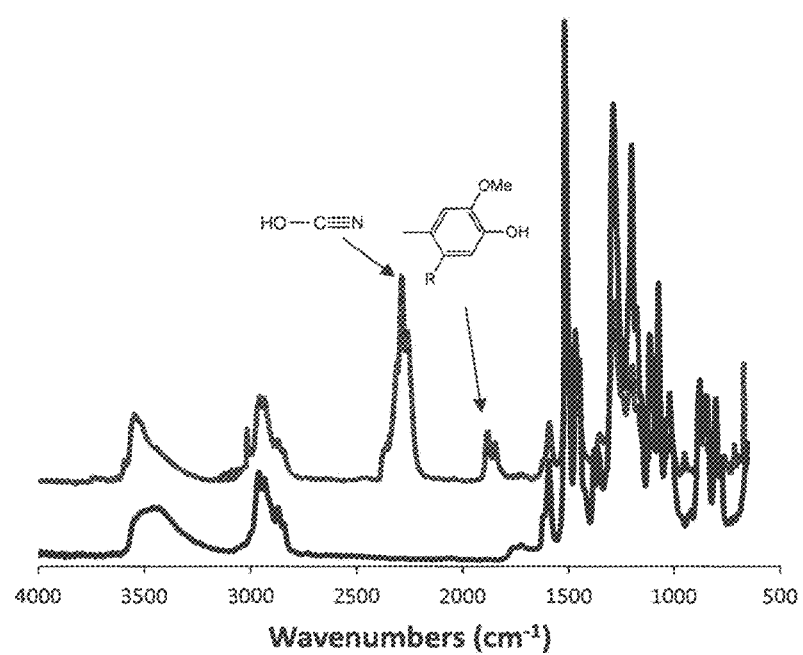
FIG. 8 is a graph showing a comparison of FTIR data for compound 4 and the pyrolysis products observed from the thermoset derived from 8 at 400° C., according to embodiments of the invention.

FIG. 8. Comparison of FTIR data for 4 and the pyrolysis products observed from the thermoset derived from 8 at 400° C.

Scheme 8. Proposed decomposition pathway for the cured resin derived from compound 8.

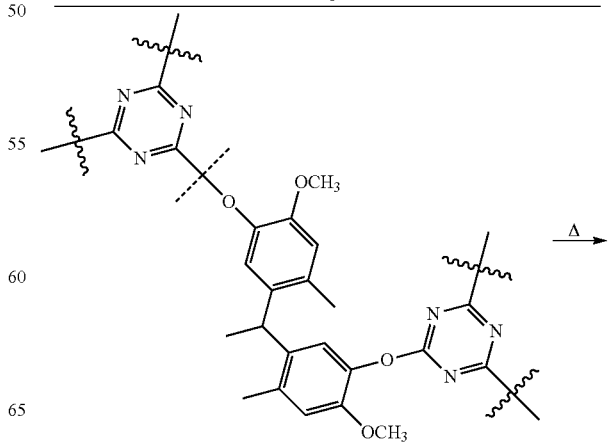

-continued

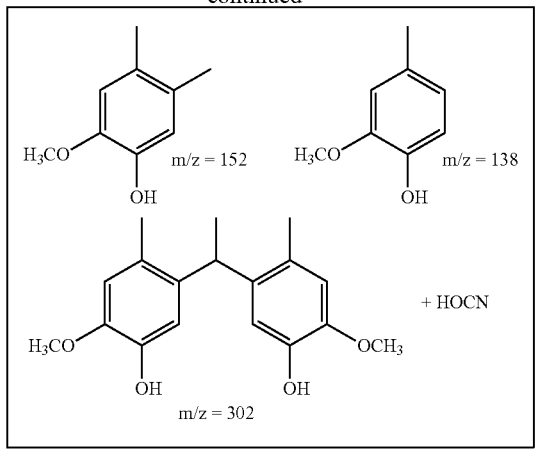

Although these initial TGA/FTIR studies provided insight into both the cure chemistry and the thermal degradation pathways of the materials, these experiments did not allow for an accurate assessment of the stability of fully cured resins. To remedy this, fragments of cured resin pucks were subjected to TGA under both a nitrogen and air atmosphere. In contrast to the TGA results for the uncured samples, no low temperature weight loss was observed due to the presence of a well-formed cyanurate ring network. Interestingly, the weight loss results were similar in both environments up to the decomposition temperature of the resins. In contrast, char yields were significantly lower in air due to oxidation and/or hydrolysis reactions. Although the char yields are somewhat low compared to conventional cyanate esters, this is to be expected due to the lower proportion of aromatic carbons in the renewable resins. Considering loss of all the functional groups except aromatic carbons, a theoretical maximum for char yield is in the range of 39-43% for these resins. The experimental char yield varies from 27-35% (Table 9) with 7 producing 81% of the theoretical char and 9 producing 69% of the theoretical char. These numbers are in relatively good agreement to BADCy (78% of theoretical), but deviate significantly from LECy (94% of theoretical) (Ramirez, M. L.; Walters, R.; Savitski, E. P.; Lyon, R. E. *Thermal Decomposition of Cyanate Ester Resins* DOT/FAA Report AR-01/32 2001). In the case of 6-9, but also for conventional cyanate esters such as BADCy, some of the loss of char yield is due to evolution of phenolics during decomposition. For 6-9, the char yield in air decreases to roughly 10% at 600° C. for all of the resins, but whether this drop is caused by oxidation chemistry or hydrolysis reactions is unclear.

TABLE 9

TGA Data for Cured Resin Pucks

| Compound | $T_{5\% \, loss}$ in $N_2$ (air), ° C. | $T_{10\% \, loss}$ in $N_2$ (air), ° C. | Char yield at 600° C. in $N_2$ (air), % |
| --- | --- | --- | --- |
| 1 | 317 (326) | 326 (339) | 33 (8) |
| 2 | 360 (357) | 366 (362) | 35 (11) |
| 3 | 330 (337) | 344 (349) | 28 (11) |
| 4 | 329 (346) | 345 (357) | 27 (11) |

From a renewable standpoint, the evolution of phenols is quite intriguing and suggests that these resins may potentially be recycled to phenols that could be utilized as precursors to future cyanate esters or a host of other industrial applications. The other main product of the decomposition, isocyanic acid, can be allowed to react with water to produce CO2 and NH3. Although beyond the scope of the current work, one could envision a pyrolitic recycling process (Scheme 9) for out-of-service composite parts fabricated from these cyanate esters. Introduction of stoichiometric water vapor at elevated temperature and under a nitrogen atmosphere would be expected to maximize the formation of phenols, resulting in truly sustainable/renewable materials.

Scheme 9. Proposed recycling pathway for renewable cyanate ester resins.

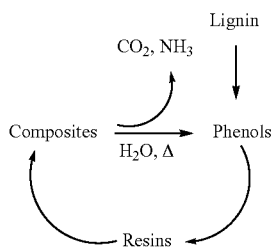

Although the primary focus of this work was to synthesize and evaluate a series of renewable cyanate esters, the results are interesting from other perspectives as well. First, the majority of conventional bisphenols used for the synthesis of epoxy and cyanate ester resins have bridging groups para to the phenol (p,p-phenols), whereas phenols with bridging groups meta to the phenol (m,m-phenols) are almost nonexistent in the literature. This work provides some rare insight into the cure behavior of both m,m- and o,o-resins. Second, most commercial resins are derived from bisphenols with no heteroatoms, while the resins discussed in this work contain electron donating methoxy-groups groups ortho to the cyanate ester. Despite differences in the cure chemistry and slightly lower thermal stability, the resins described in this work performed remarkably well considering the structural and electronic differences between these and conventional resins. Third, the potential to recycle thermosetting resins could be of great benefit to society from economical, environmental, and logistical perspectives. Although the current efforts have merely broached the subject, the study of how atypical substituents, such as methoxy groups, affect the decomposition of thermosetting resins could lead to the design of high performance composites that are suitable for use in a variety of applications and environments, but can be easily recycled by thermal and/or chemical methods.

Prophetic Examples

Any of the prophetic examples are for illustration purposes only and not to be used to limit any of the embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other slated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method of synthesizing modified renewable bio-polyphenols, comprising:
   condensing one equivalent of an aldehyde and/or ketone with two equivalents of at least one renewable phenol and utilizing at least one dilute mineral acid or heterogeneous solid acid catalyst to produce renewable bio-polyphenols; and
   modifying said renewable bio-polyphenols with sulfonates, followed by reductive elimination and/or hydrolysis;
   wherein said sulfonates comprises at least one of mesylate and triflate.

2. The method according to claim 1, wherein said at least one renewable phenol is selected from the group consisting of creosol (2-methoxy-4-methylphenol), guaiacol (2-methoxyphenol), ortho-cresol, para-cresol, meta-cresol, and combination thereof.

3. The method according to claim 1, wherein said heterogeneous solid acid catalyst comprises at least one Bronsted and/or Lewis acid site.

4. Modified bio-polyphenols produced by the method of claim 1.

5. Blends comprising two or more of said modified renewable bio-polyphenols produced by the method of claim 1.

6. The method according to claim 1, further comprising converting said modified renewable bio-polyphenols into polymers selected from cyanate esters, epoxides, polyesters, polysulfones, polyester-styrene, alkylphenolic polymers, polyoxalates, and polyalylates.

7. The method according to claim 1, further comprising converting said modified renewable bio-polyphenols to polycarbonates with Mn ranging from 1000 to 10,000,000 g/mol utilizing reagents including organic carbonates and a Lewis acid catalyst, phosgene and phosgene surrogates.

8. Polycarbonates produced by the method of claim 7.

9. The method according to claim 1, further comprising converting said modified renewable bio-polyphenols into resins selected from cyanate esters, epoxides, polyesters, polysulfones, polyester-styrene, alkylphenolic polymers, polyoxalates, and polyalylates.

10. Cyanate esters or epoxy resins produced by the method of claim 9.

11. The method according to claim 9, further comprising cross-linking said resins by thermal or chemical methods or with irradiation, to produce high molecular weight cross-linked thermoplastic polymers.

12. The method according to claim 11, further comprising blending said cross-linked polymers with at least one support material selected from polymers, glass, carbon, metals, silica, clays, metal oxides, carbon nanotubes, graphenes, and nanostructured materials; and curing to produce a composite material.

13. High molecular weight thermoplastics produced by the method of claim 11.

14. The method according to claim 11, further comprising blending said cross-linked polymers with at least one support material selected from glass, carbon, metals, silica, clays, metal oxides, carbon nanotubes, graphenes, and nanostructured materials; and curing to produce composite materials.

15. Composite materials produced by the method of claim 14.

16. The method according to claim 9, further comprising blending said resins with at least one fibrous material selected from glass, carbon, polymer, and carbon nanotubes, or with at least one non-fibrous material selected from metal, silica, clay, metal oxide, graphenes, and nanostructured materials, to produce a mixture; and curing said mixture to produce composite materials.

17. Composite materials produced by the method of claim 16.

* * * * *